US010729573B2

(12) United States Patent
Stangenes et al.

(10) Patent No.: US 10,729,573 B2
(45) Date of Patent: *Aug. 4, 2020

(54) PYLORIC ANCHORS AND METHODS FOR INTESTINAL BYPASS SLEEVES

(71) Applicant: METAMODIX, INC., Plymouth, MN (US)

(72) Inventors: Todd Stangenes, Minneapolis, MN (US); Werner Schwarz, Ruhpolding (DE); Kedar R. Belhe, Minnetonka, MN (US); Mathew Ziebol, Blaine, MN (US); Edward Anderson, Maple Grove, MN (US)

(73) Assignee: MetaModix, Inc., Plymouth, MN (US)

( * ) Notice: Subject to any disclaimer, the term of this patent is extended or adjusted under 35 U.S.C. 154(b) by 164 days.

This patent is subject to a terminal disclaimer.

(21) Appl. No.: 15/489,444

(22) Filed: Apr. 17, 2017

(65) Prior Publication Data

US 2017/0252195 A1    Sep. 7, 2017

Related U.S. Application Data

(63) Continuation of application No. 15/060,418, filed on Mar. 3, 2016, now Pat. No. 9,622,897.

(51) Int. Cl.
*A61M 25/04* (2006.01)
*A61F 5/00* (2006.01)

(52) U.S. Cl.
CPC .......... *A61F 5/0079* (2013.01); *A61F 5/0003* (2013.01); *A61F 5/0036* (2013.01); *A61F 5/0076* (2013.01); *A61M 25/04* (2013.01)

(58) Field of Classification Search
CPC ............................ A61F 5/0076; A61F 5/0079
See application file for complete search history.

(56) References Cited

U.S. PATENT DOCUMENTS

| 4,134,405 A | 1/1979 | Smit |
| 4,204,530 A | 5/1980 | Finney |

(Continued)

FOREIGN PATENT DOCUMENTS

| AU | 2006227471 B2 | 9/2006 |
| AU | 2014200766 B2 | 6/2015 |

(Continued)

OTHER PUBLICATIONS

Buchwald, Henry et al., "Bariatric Surgery: A Systematic Review and Meta-Analysis", JAMA, Oct. 13, 2004, 292 (14), pp. 1724-1737.

(Continued)

*Primary Examiner* — Kai H Weng
(74) *Attorney, Agent, or Firm* — Faegre Drinker Biddle & Reath LLP

(57) ABSTRACT

A gastrointestinal device for implanting within a patient's gastrointestinal tract, the device having a central axis and a first expandable portion comprising a hollow tubular braided structure of wire and having a first cylinder extending parallel to the central axis, the first cylinder having a length and a first face; a neck portion extending from the first face of the first expandable portion parallel to the central axis, the neck portion having a first end, a second end, a wall extending between the first end and second end, and a diameter sized to fit within a pylorus; and a second expandable portion comprising a hollow tubular braided structure of wire and having a second cylinder extending parallel to the central axis, the second cylinder having a second face located at the proximal end of the second cylinder and oriented transverse to the central axis.

20 Claims, 34 Drawing Sheets

(56) References Cited

U.S. PATENT DOCUMENTS

| | | |
|---|---|---|
| 4,246,893 A | 1/1981 | Berson |
| 4,314,405 A | 2/1982 | Park |
| 4,315,509 A | 2/1982 | Smit |
| 4,416,267 A | 11/1983 | Garren et al. |
| 4,501,264 A | 2/1985 | Rockey |
| 4,641,653 A | 2/1987 | Rockey |
| 4,716,900 A | 1/1988 | Ravo et al. |
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,480,423 A | 1/1996 | Ravenscroft et al. |
| 5,749,921 A | 5/1998 | Lenker et al. |
| 5,753,253 A | 5/1998 | Meyer |
| 5,755,769 A | 5/1998 | Richard et al. |
| 5,820,584 A | 10/1998 | Crabb |
| 5,824,040 A | 10/1998 | Cox et al. |
| 6,017,563 A | 1/2000 | Knight et al. |
| 6,224,627 B1 | 5/2001 | Armstrong et al. |
| 6,267,988 B1 | 7/2001 | Meyer |
| 6,368,617 B1 | 4/2002 | Hastings et al. |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,676,674 B1 | 1/2004 | Dudai |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Levine et al. |
| 8,105,392 B2 | 1/2012 | Durgin |
| 8,114,045 B2 | 2/2012 | Surti |
| 8,182,441 B2 | 5/2012 | Swain et al. |
| 8,183,441 B2 | 5/2012 | Cukadar |
| 8,211,186 B2 | 7/2012 | Belhe et al. |
| 8,282,598 B2 | 10/2012 | Belhe et al. |
| 8,579,849 B2 | 11/2013 | Grau et al. |
| 8,702,641 B2 | 4/2014 | Belhe et al. |
| 8,702,642 B2 | 4/2014 | Belhe et al. |
| 8,882,698 B2 | 11/2014 | Levine et al. |
| 9,044,300 B2 | 6/2015 | Belhe et al. |
| 9,173,760 B2 | 11/2015 | Belhe et al. |
| 9,278,019 B2 | 3/2016 | Thompson et al. |
| 9,622,897 B1 | 4/2017 | Stangenes et al. |
| 9,962,278 B2 | 5/2018 | Belhe et al. |
| 10,159,699 B2 | 12/2018 | Belhe et al. |
| 10,322,021 B2 | 6/2019 | Belhe et al. |
| 2002/0183768 A1 | 12/2002 | Deem et al. |
| 2002/0188354 A1 | 12/2002 | Peghini |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1 | 5/2004 | Kagan et al. |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |

(56) References Cited

U.S. PATENT DOCUMENTS

| | | |
|---|---|---|
| 2005/0022827 A1 | 2/2005 | Woo et al. |
| 2005/0033226 A1 | 2/2005 | Kim |
| 2005/0033331 A1 | 2/2005 | Burnett et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0036267 A1 | 2/2006 | Saadat et al. |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0156248 A1 | 7/2007 | Marco et al. |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221595 A1 | 9/2008 | Surti |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0110664 A1 | 4/2009 | Moore |
| 2009/0118749 A1 | 5/2009 | Shalon et al. |
| 2009/0125119 A1 | 5/2009 | Obermiller et al. |
| 2009/0138094 A1 | 5/2009 | Schurr |
| 2009/0149871 A9 | 6/2009 | Kagan et al. |

(56) References Cited

U.S. PATENT DOCUMENTS

| | | |
|---|---|---|
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0114130 A1 | 5/2010 | Meade et al. |
| 2010/0135971 A1 | 6/2010 | Schiffrin |
| 2010/0191170 A1 | 7/2010 | Chang |
| 2010/0256775 A1 | 10/2010 | Belhe et al. |
| 2010/0305590 A1 | 12/2010 | Holmes et al. |
| 2011/0004320 A1 | 1/2011 | Priplata et al. |
| 2011/0009690 A1 | 1/2011 | Belhe et al. |
| 2011/0054493 A1 | 3/2011 | McLean et al. |
| 2011/0104327 A1 | 5/2011 | Kirejevas |
| 2011/0106273 A1 | 5/2011 | Belhe et al. |
| 2011/0306544 A1 | 12/2011 | Sukhotnik et al. |
| 2012/0065571 A1 | 3/2012 | Thompson et al. |
| 2012/0109188 A1 | 5/2012 | Viola |
| 2012/0136457 A1 | 5/2012 | Grau et al. |
| 2012/0184893 A1 | 7/2012 | Thompson et al. |
| 2012/0184967 A1 | 7/2012 | Levine et al. |
| 2012/0232460 A1 | 9/2012 | Raven et al. |
| 2012/0253259 A1 | 10/2012 | Belhe et al. |
| 2012/0253260 A1 | 10/2012 | Belhe et al. |
| 2012/0302936 A1 | 11/2012 | Belhe et al. |
| 2013/0013084 A1 | 1/2013 | Birk |
| 2013/0030351 A1 | 1/2013 | Belhe et al. |
| 2013/0324907 A1 | 12/2013 | Huntley et al. |
| 2014/0194806 A1 | 7/2014 | Belhe et al. |
| 2014/0200502 A1 | 7/2014 | Belhe et al. |
| 2014/0213960 A1 | 7/2014 | Belhe et al. |
| 2014/0309576 A1 | 10/2014 | Belhe et al. |
| 2014/0350694 A1 | 11/2014 | Behan |
| 2014/0379093 A1 | 12/2014 | Durgin |
| 2015/0313740 A1 | 11/2015 | O'Neill et al. |
| 2016/0089256 A1 | 3/2016 | Belhe et al. |
| 2016/0228276 A1 | 8/2016 | Thompson et al. |
| 2019/0060375 A1 | 2/2019 | Belhe et al. |
| 2020/0000616 A1 | 1/2020 | Belhe et al. |

FOREIGN PATENT DOCUMENTS

| | | |
|---|---|---|
| CN | 1575155 A | 2/2005 |
| CN | 1618411 A | 5/2005 |
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1881781 A2 | 1/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| EP | 2945566 A1 | 11/2015 |
| JP | 2005500127 A | 1/2005 |
| JP | 2007513684 A | 5/2007 |
| JP | 2007513685 A1 | 5/2007 |
| WO | WO1998049943 A2 | 11/1998 |
| WO | WO2002096327 A2 | 12/2002 |
| WO | WO2003017882 A2 | 3/2003 |
| WO | WO2003086246 A1 | 10/2003 |
| WO | WO2003086247 A1 | 10/2003 |
| WO | WO2003094785 A1 | 11/2003 |
| WO | WO2004011085 A1 | 2/2004 |
| WO | WO2004017863 A2 | 3/2004 |
| WO | WO2004041133 A1 | 5/2004 |
| WO | WO2004064680 A1 | 8/2004 |
| WO | WO2004064685 A1 | 8/2004 |
| WO | WO2004087014 A2 | 10/2004 |
| WO | WO2004087233 A2 | 10/2004 |
| WO | WO2004049982 B1 | 12/2004 |
| WO | WO2005037152 A1 | 4/2005 |
| WO | WO2005058415 A2 | 6/2005 |
| WO | WO2005060869 A2 | 7/2005 |
| WO | WO2005060882 A1 | 7/2005 |
| WO | WO2005065412 A2 | 7/2005 |
| WO | WO2005097012 A2 | 10/2005 |
| WO | WO2005099591 A2 | 10/2005 |
| WO | WO2005110244 A1 | 11/2005 |
| WO | WO2005110280 A2 | 11/2005 |
| WO | WO2005112822 A1 | 12/2005 |
| WO | WO2005120363 A1 | 12/2005 |
| WO | WO2006014496 A2 | 2/2006 |
| WO | WO2006016894 A1 | 2/2006 |
| WO | WO2006020370 A2 | 2/2006 |
| WO | WO2006028898 A2 | 3/2006 |
| WO | WO2006034062 A1 | 3/2006 |
| WO | WO2006060049 A2 | 6/2006 |
| WO | WO2006062996 A2 | 6/2006 |
| WO | WO2006078781 A1 | 7/2006 |
| WO | WO2006078927 A2 | 7/2006 |
| WO | WO2006102012 A1 | 9/2006 |
| WO | WO2006102240 A2 | 9/2006 |
| WO | WO2006124880 A2 | 11/2006 |
| WO | WO2006127593 A2 | 11/2006 |
| WO | WO2006133311 A2 | 12/2006 |
| WO | 2007/001468 | 1/2007 |
| WO | WO2007019117 A1 | 2/2007 |
| WO | WO2007030829 A2 | 3/2007 |
| WO | WO2007038715 A1 | 4/2007 |
| WO | WO2007041598 A2 | 4/2007 |
| WO | WO2007075396 A2 | 7/2007 |
| WO | WO2007092390 A2 | 8/2007 |
| WO | WO2007107990 A2 | 9/2007 |
| WO | WO2007127209 A2 | 11/2007 |
| WO | WO2007136468 A2 | 11/2007 |
| WO | WO2007139920 A2 | 12/2007 |
| WO | WO2007142829 A1 | 12/2007 |

(56) References Cited

FOREIGN PATENT DOCUMENTS

| WO | WO2007142832 A1 | 12/2007 |
|---|---|---|
| WO | WO2007142833 A1 | 12/2007 |
| WO | WO2007142834 A1 | 12/2007 |
| WO | WO2007145684 A2 | 12/2007 |
| WO | WO2008005510 A2 | 1/2008 |
| WO | WO2008030403 A1 | 3/2008 |
| WO | WO2008033409 A1 | 3/2008 |
| WO | WO2008033474 A2 | 3/2008 |
| WO | WO2008039800 A2 | 4/2008 |
| WO | WO2008101048 A2 | 8/2008 |
| WO | WO2008106041 A1 | 9/2008 |
| WO | WO2008106279 A1 | 9/2008 |
| WO | WO2008112942 A2 | 9/2008 |
| WO | WO2008127552 A2 | 10/2008 |
| WO | WO2008141288 A1 | 11/2008 |
| WO | WO2008148047 A2 | 12/2008 |
| WO | WO2008150905 A1 | 12/2008 |
| WO | WO2008154450 A1 | 12/2008 |
| WO | WO2008154594 A2 | 12/2008 |
| WO | WO2009011881 A1 | 1/2009 |
| WO | WO2009011882 A2 | 1/2009 |
| WO | WO2009012335 A1 | 1/2009 |
| WO | WO2009036244 A1 | 3/2009 |
| WO | WO2009046126 A1 | 4/2009 |
| WO | WO2009082710 A1 | 7/2009 |
| WO | WO2009085107 A1 | 7/2009 |
| WO | WO2009086549 A1 | 7/2009 |
| WO | WO2009097582 A1 | 8/2009 |
| WO | WO2009097585 A1 | 8/2009 |
| WO | WO2010115011 A1 | 10/2010 |
| WO | WO2011062882 A1 | 5/2011 |
| WO | WO2011073970 A1 | 6/2011 |
| WO | WO2011099940 A8 | 8/2011 |
| WO | WO2012103531 A2 | 8/2012 |
| WO | 2014113483 A1 | 7/2014 |
| WO | 2015138465 A1 | 9/2015 |

OTHER PUBLICATIONS

Daniels, Stephen, "Probiotics may 'counter obesity and diabetes': NIH study", Jul. 10, 2013, downloaded from http://www.nutraingredients-usa.com/research/probiotics-may-counter-obesity-and-diabetes-NIH-study, 2 pages.
International Search Report and Written Opinion issued in PCT/US2011/061193.
Ley, Ruth E. et al., "Microbial ecology: human gut microbes associated with obesity", Nature, vol. 44, No. 7122, pp. 1022-1023, 2006.
Partial European Search Report issued in EP14172564, dated Feb. 12, 2015, 7pages.
Pories, Walter J. et al., "Surgical Treatment of Obesity and its Effect on Diabetes: 10-6 Follow-up", Am J Clin Nutr 1992, 55, 582S-585S.
Pories, Walter J. et al., "Who Would Have Thought It? An Operation Proves to be the Most Effective Therapy for Adult-Onset Diabetes Mellitus", Annals of Surgery, Sep. 1995, 222(3), pp. 339-352.
Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.
Rubino, Francesco et al., "Potential of Surgery for Curing Type 2 Diabetes Mellitus", Annals of Surgery, Nov. 2002, 236(5), 554-559.
Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.
Strader, April et al., "Weight Loss Through Ileal transposition is accompanied by increased ileal hormone secretion and synthesis in rats", Am J Physiol Endocrinol Metab 288: E447-E453, 2005.
Supplemental European Search Report issued in EP Application 14740554 dated Sep. 26, 2016, 7 pages.
Troy, Stephanie et al., "Intestinal Gluconeogenesis is a key factor for early metabolic changes after gastric bypass but not after gastric lap-band in mice", Cell metabolism 8, 201-211, Sep. 3, 2008.
U.S. Appl. No. 15/060,418 entitled Pyloric Anchors and Methods for Intestinal Bypass Sleeves filed Mar. 3, 2016.
Vetter, Marion et al., "Narrative Review: Effect of bariatric Surgery on Type 2 Diabetes Mellitus", Annals of Internal Medicine, Jan. 20, 2009, 150(2), pp. 94-104.
Woodard et al., Probiotics Improve Outcomes After Roux-en-Y Gastric Bypass Surgery: A Prospective Randomized Trial, J Gastrointest Surg (2009) 13:1198-1204.
Yadav, Hariom et al., Beneficial Metabolic Effects of a Probiotic via Butyrate-induced GLP-1 Hormone Secretion, Journal of Biological Chemistry, 2013, vol. 288, pp. 25088-25097.
Better Nutrition: Your guide to Natural Living, Bouncing Back (http://www.betternutrition.com/natural-surgery-recovery-antiobiotics-pro- biotics/), Sep. 2009, accessed Jun. 14, 2016.
Cummings, David E. et al., "Role of the bypassed proximal intestine in the antidiabetic effects of bariatric surgery", Surgery for Obesity and Related Diseases 3 2007, pp. 109-115.
Extended European Search Report issued in EP Application No. 12739077.1, dated Nov. 16, 2017, 6 pages.
Gavitt et al., Probiotics Improve Outcomes After Roux-en-Y Gastric Bypass Surgery: A Prospective Randomized Trial, J Gastrointest Surg (2009) 13:1198-1204.
International Preliminary Report on Patentability issued in PCT/US2014/011702, dated Jul. 30, 2015, 7 pages.
International Preliminary Report on Patentability received for PCT Patent Application No. PCT/US10/29648, dated Oct. 13, 2011, 12 pages.
International Preliminary Report on Patentability received for PCT Patent Application No. PCT/US10/41574, dated Jan. 19, 2012, 8 pages.
International Preliminary Report on Patentability received for PCT Patent Application No. PCT/US11/61193, dated May 30, 2013, 10 pages.
International Preliminary Report on Patentability received for PCT Patent Application No. PCT/US2012/023048, dated Sep. 19, 2013, 9 pages.
International Preliminary Report on Patentability received for PCT Patent Application No. PCT/US2017/020494, dated Sep. 13, 2018, 6 pages.
International Search Report and Written Opinion issued in PCT/US12/58202, dated Jan. 23, 2013, 14 pages.
International Search Report and Written Opinion issued in PCT/US2010/029648, dated Aug. 24, 2010.
International Search Report and Written Opinion issued in PCT/US2010/041574, dated Jan. 25, 2011.
International Search Report and Written Opinion issued in PCT/US2011/020560, dated Mar. 28, 2011, 10 pages.
International Search Report and Written Opinion issued in PCT/US2012/023048, dated Jun. 22, 2012.
International Search Report and Written Opinion issued in PCT/US2014/011702, dated Mar. 21, 2014, 9 pages.
International Search Report and Written Opinion issued in PCT/US2015/019730, dated Mar. 10, 2015, 15 pages.
International Search Report and Written Opinion issued in PCT/US2017/020494, dated Apr. 3, 2017, 10 pages.
Invitation to Pay Additional Fees issued in PCT/US2010/029648, dated Jun. 1, 2010.
Parnell, Jill k, et al. "Prebiotic Fiber Modulation of the Gut Microbiota Improves Risk Factors for Obesity and the Metabolic Syndrome." Gut Microbes, 3(1):29-34, Jan. 1, 2012.
Pories, Walter J. et al., "Who Would Have Thought It? an Operation Proves to be the Most Effective Therapy for Adult-Onset Diabetes Mellitus", Annals of Survery, Sep. 1995, 222(3), pp. 339-352.
Preliminary Report on Patentability issued in PCT/US2015/019730 dated Sep. 22, 2016, 7 pages.
Probiotics may improve results after weight loss surgery (http://www.malleysurgical.com/blog/85probioticsmayimproveresultsafterweightloss, published Oct. 29, 2012, accessed Feb. 10, 2017).

(56) References Cited

OTHER PUBLICATIONS

Rodriguez-Grunert, Leonardo et al., "First Human Experience With endoscopically Delivered and retrieved duodenal-jejunal bypass sleeve", Surgery for Obesity and Related diseases 4 (2008) 55-59.
Schouten, Ruben et al., "A Multicenter, Randomized Efficacy Study of the endoBarrier Gastrointestinal Liner for Presurgical Weight Loss Prior to Bariatric Surgery", Annals of Surgery, vol. 251, No. 2, Feb. 2010, pp. 236-243.
Strader, Apr. et al., "Weight Loss Through Ileal transposition is accompanied by increased ileal hormone secretion and synthesis in rats", Am J Physiol Endocrinol Metab 288: E447-E453, 2005.
Supplemental European Search Report issued in EP Application 14740554 dated Sep. 2016, 7 pages.

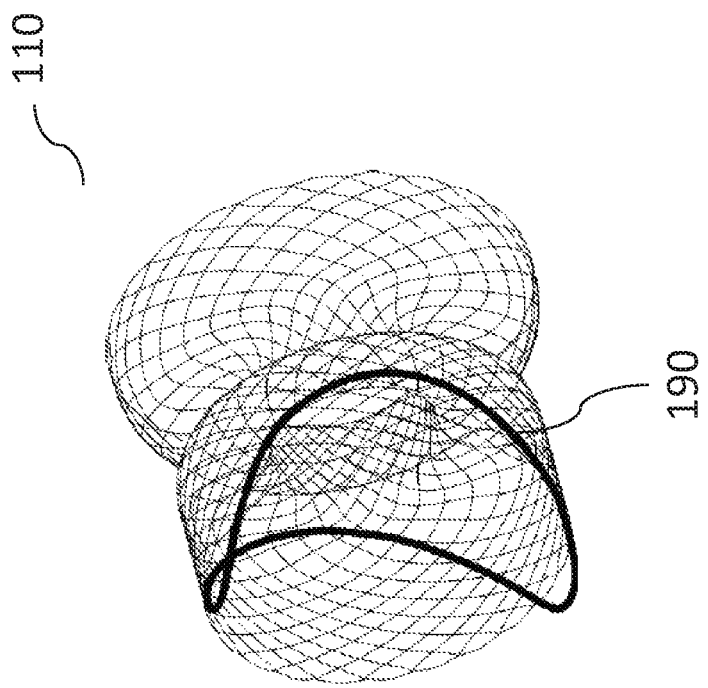
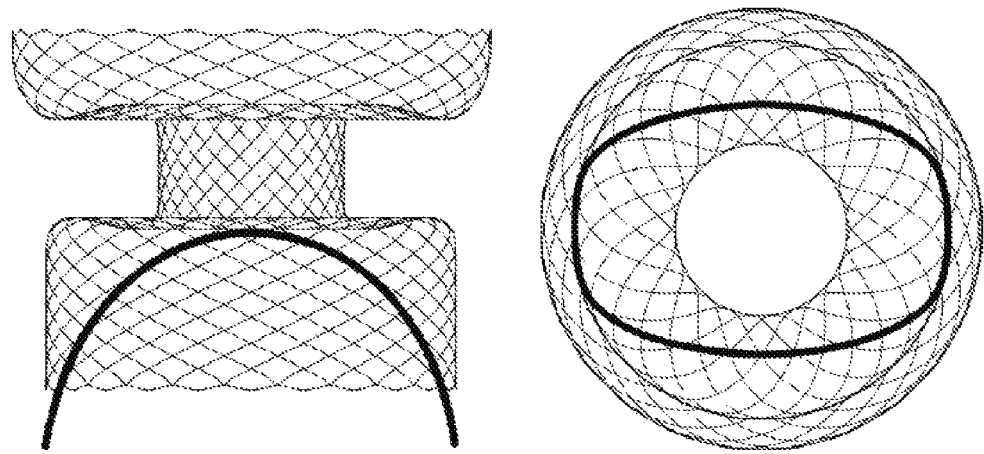
FIG. 9

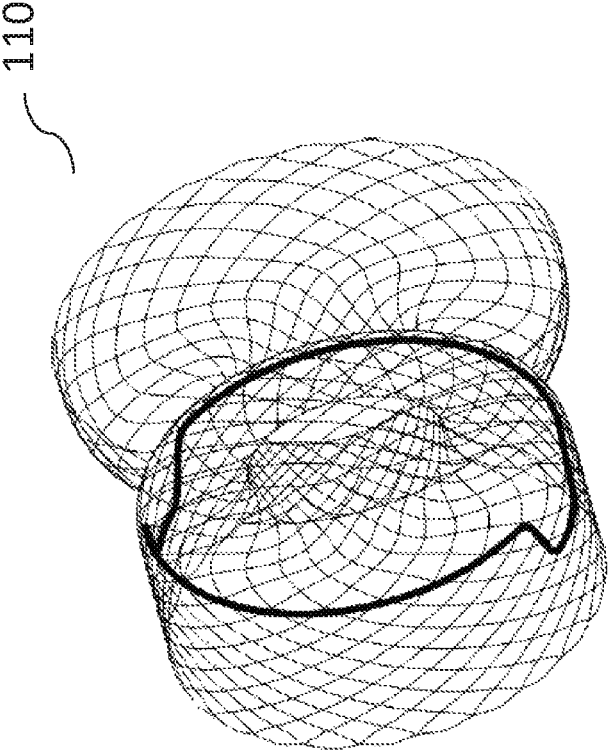
FIG. 11

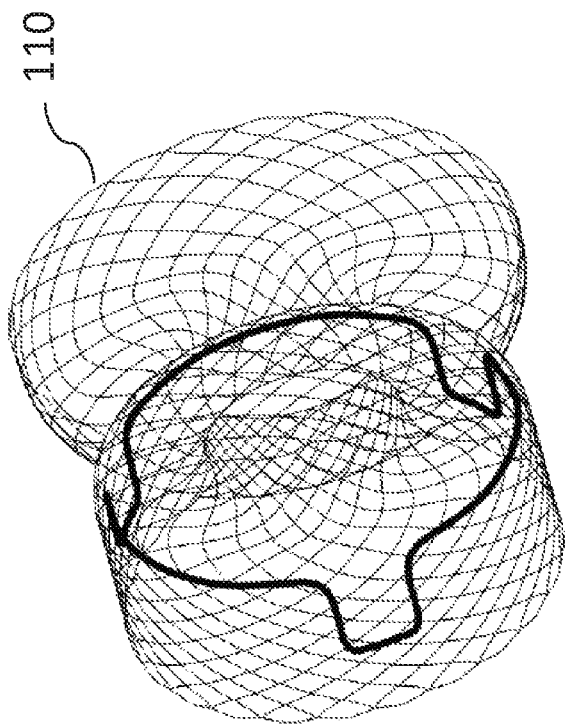
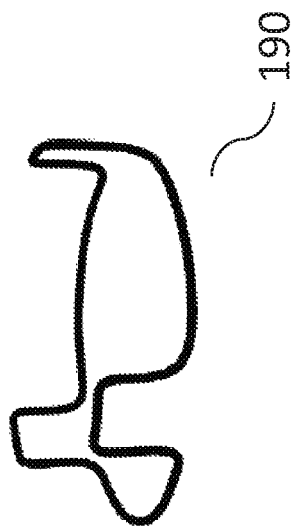
FIG. 12

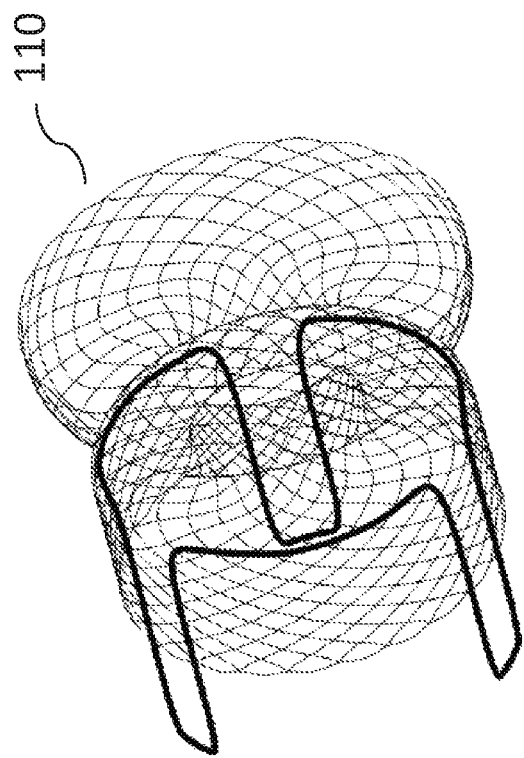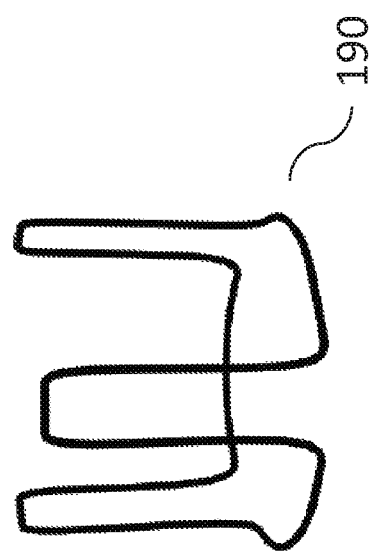
FIG. 13

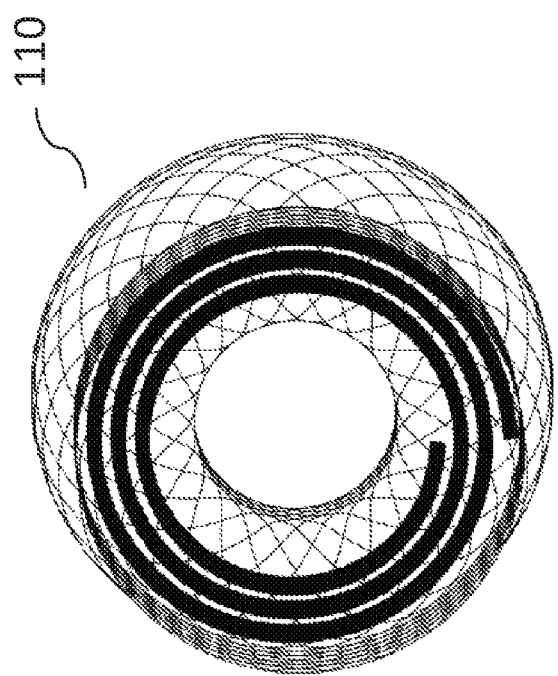
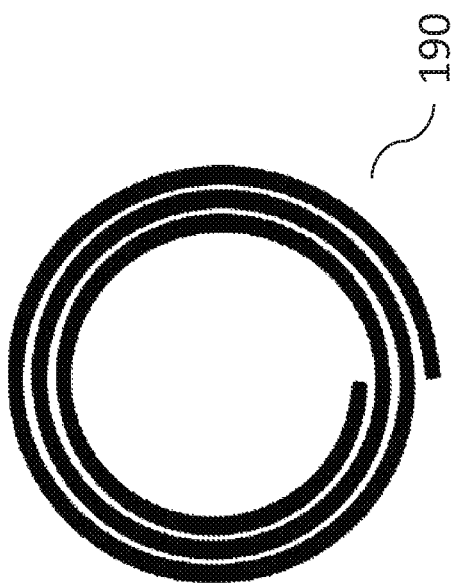
FIG. 14

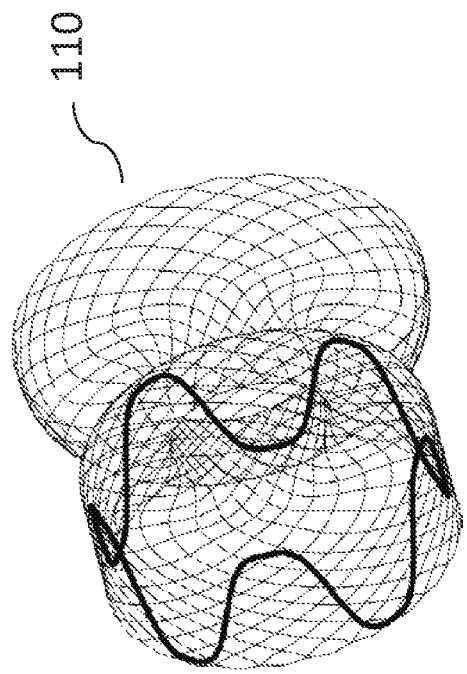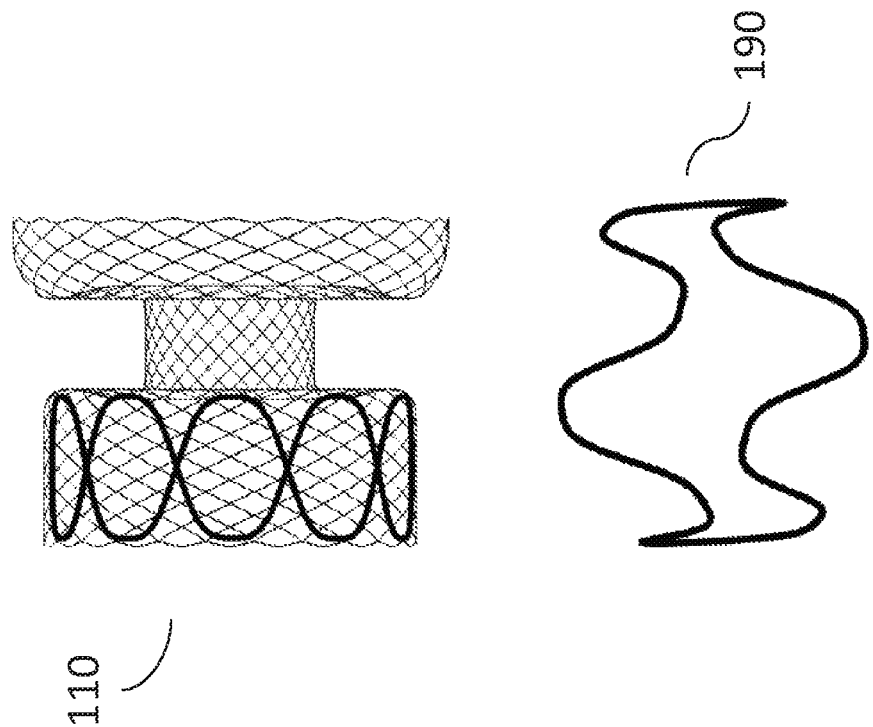
FIG. 16

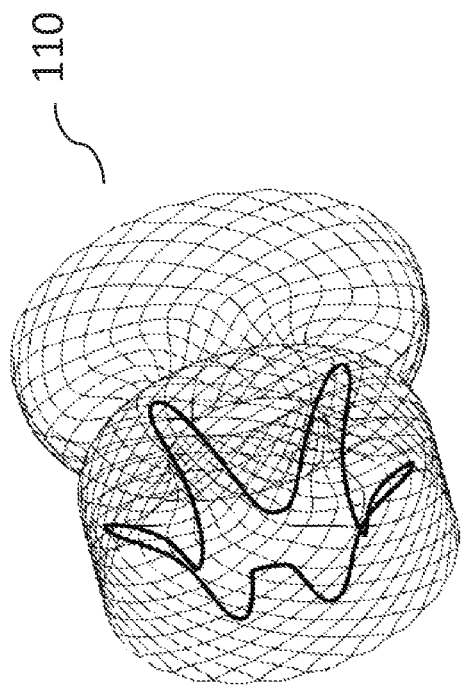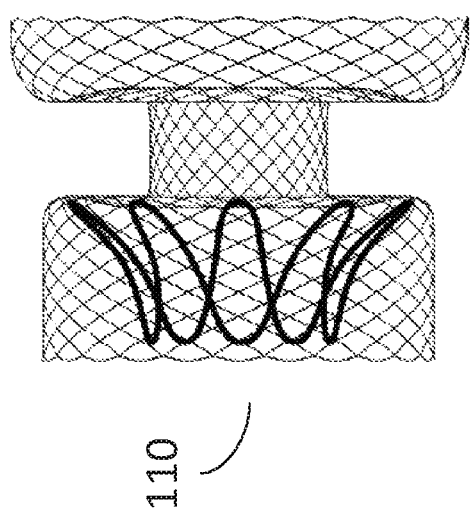
FIG. 19

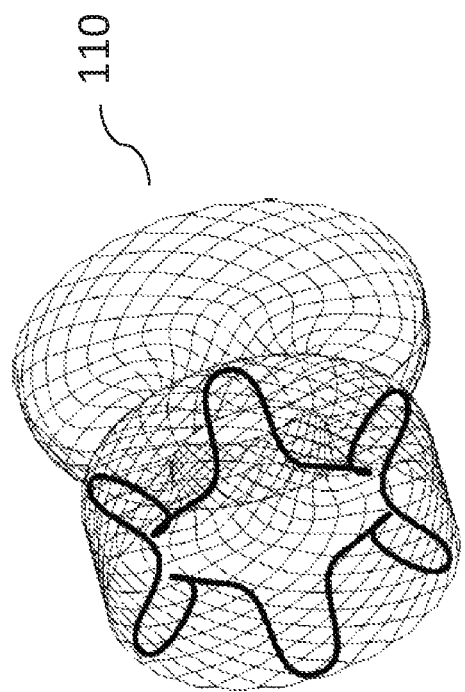
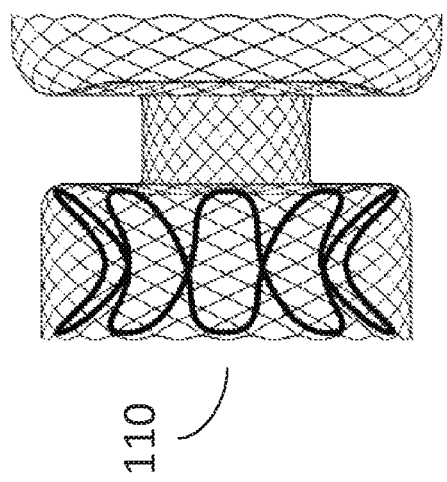
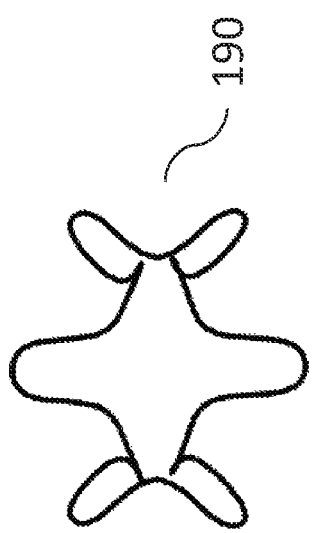
FIG. 20

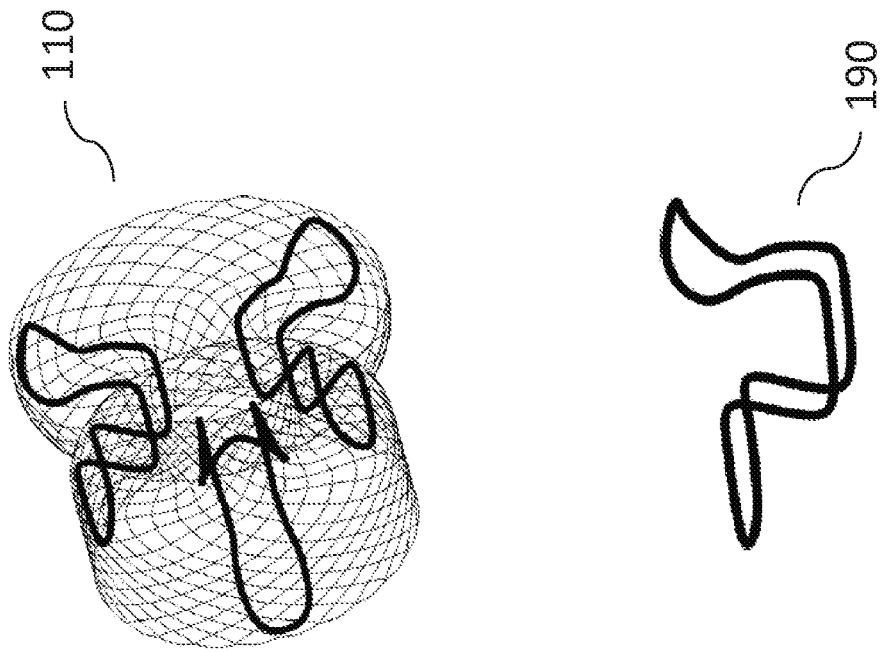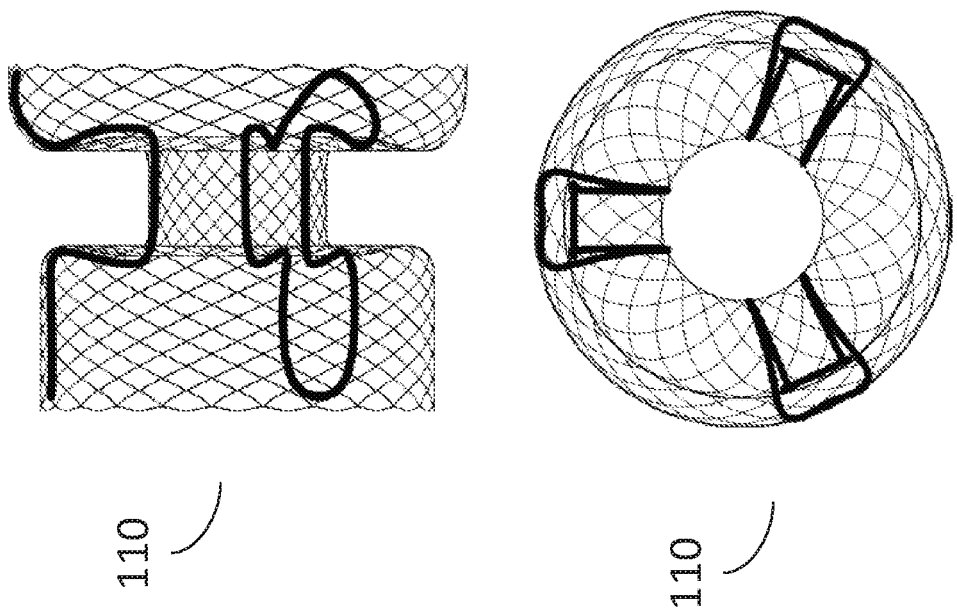
FIG. 21

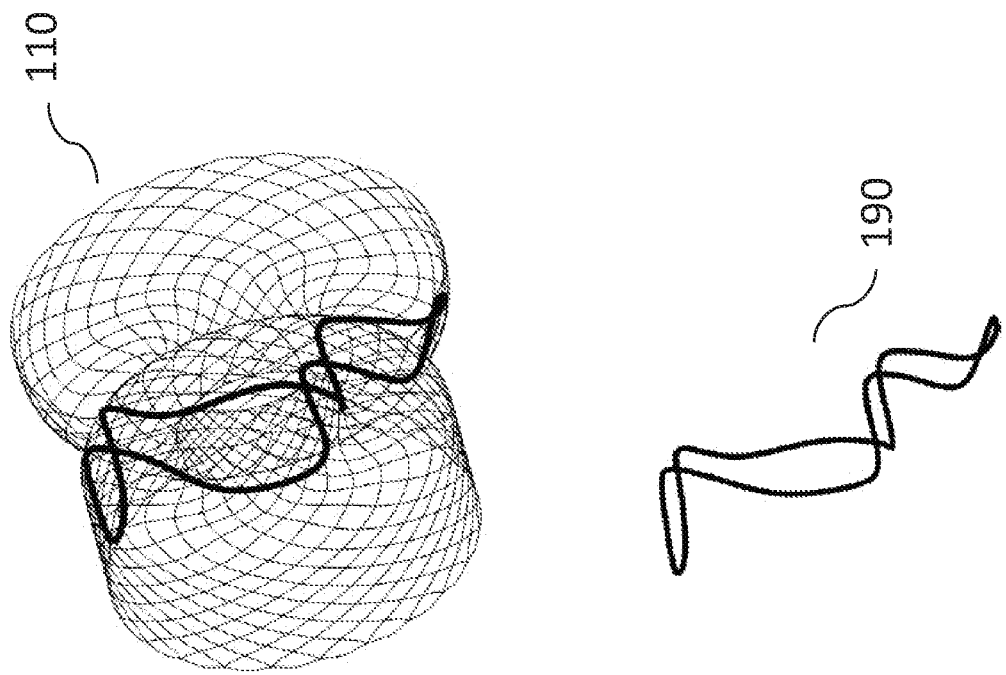
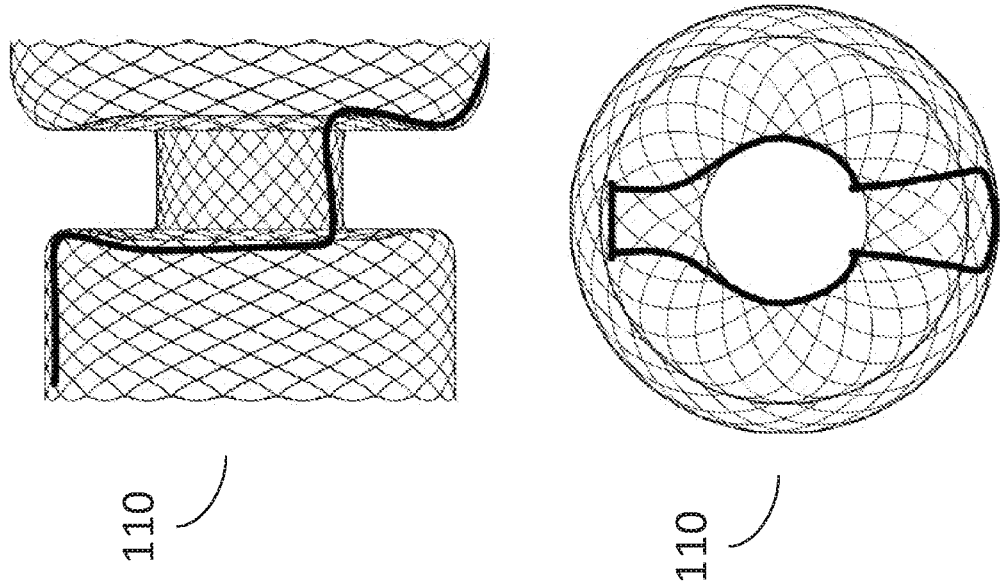
FIG. 22

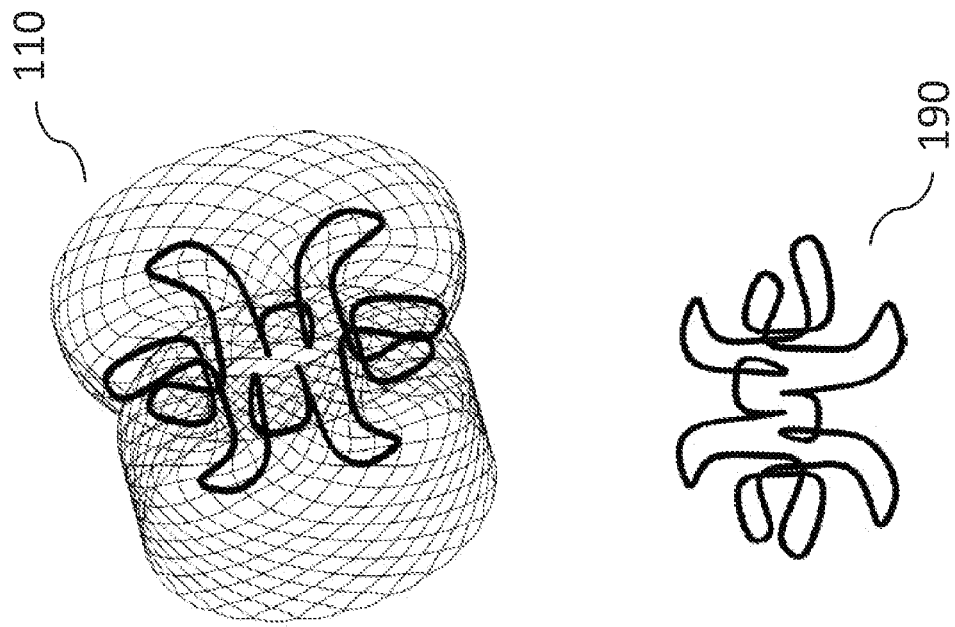
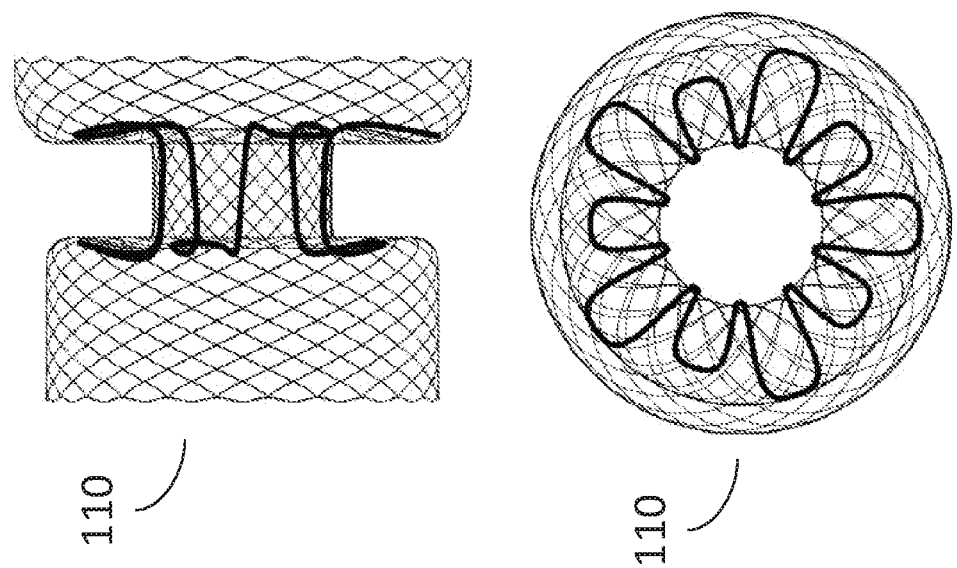
FIG. 23

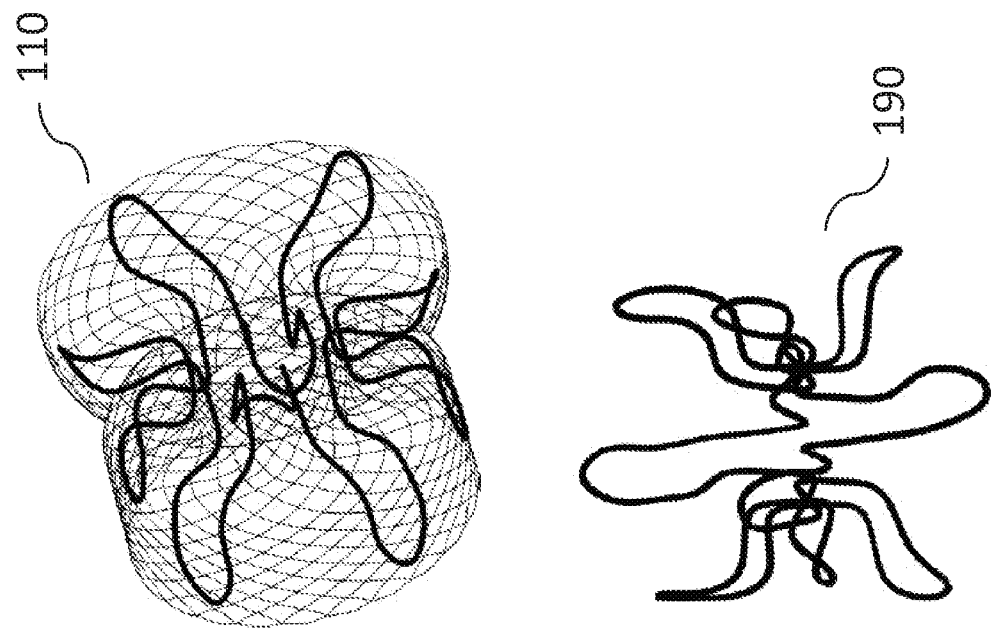
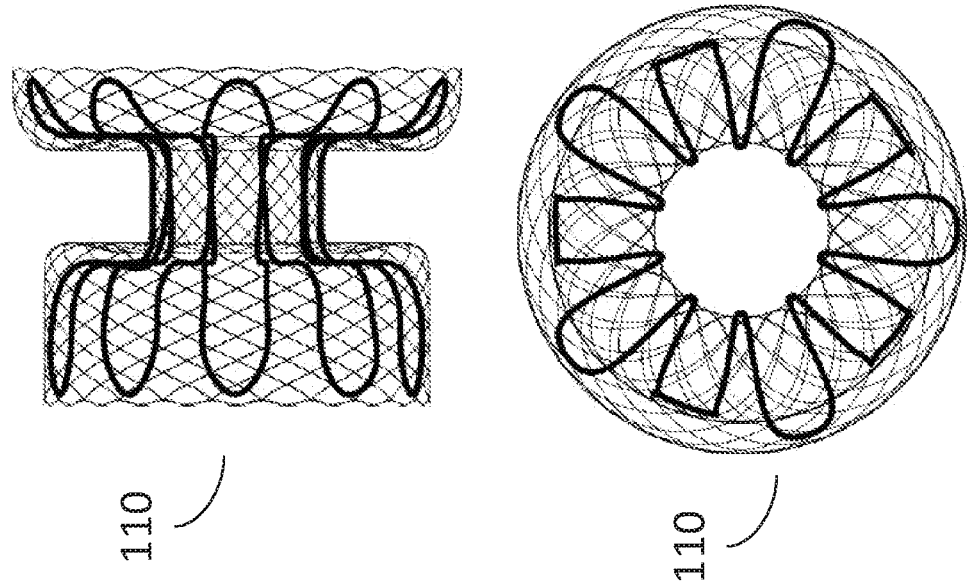
FIG. 24

PYLORIC ANCHORS AND METHODS FOR INTESTINAL BYPASS SLEEVES

PRIORITY

This application claims priority to application Ser. No. 15/060,418 filed Mar. 3, 2016, which is herein incorporated by reference in its entirety.

TECHNICAL FIELD

The instant disclosure relates generally to implants placed within gastrointestinal systems, including the esophagus, the stomach and the intestines. More particularly, it relates to devices and methods for implant systems having components implantable and removable using endoscopic techniques for treatment of obesity, diabetes, reflux, gastroparesis and other gastrointestinal conditions.

BACKGROUND

Bariatric surgery procedures, such as sleeve gastrectomy, the Roux-en-Y gastric bypass (RYGB) and the bileo-pancreatic diversion (BPD), modify food intake and/or absorption within the gastrointestinal system to effect weight loss in obese patients. These procedures affect metabolic processes within the gastrointestinal system, by either short circuiting certain natural pathways or creating different interactions between the consumed food, the digestive tract, its secretions and the neuro-hormonal system regulating food intake and metabolism. In the last few years there has been a growing clinical consensus that obese patients who undergo bariatric surgery see a remarkable resolution of their type-2 Diabetes Mellitus (T2DM) soon after the procedure. The remarkable resolution of diabetes after RYGB and BPD typically occurs too fast to be accounted for by weight loss alone, suggesting there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there has been increased effort to develop minimally invasive procedures to mimic the effects of bariatric surgery. One such procedure involves the use of gastrointestinal implants that modify transport and absorption of food and organ secretions. For example, U.S. Pat. No. 7,476,256 describes an implant having a tubular sleeve with anchoring barbs, which offer the physician limited flexibility and are not readily removable or replaceable. Moreover, stents with active fixation means, such as barbs that deeply penetrate into surrounding tissue, may potentially cause tissue necrosis and erosion of the implants through the tissue, which can lead to complications, such as bacterial infection of the mucosal tissue or systemic infection. Also, due to the intermittent peristaltic motion within the digestive tract, implants such as stents have a tendency to migrate.

Gastroparesis is a chronic, symptomatic disorder of the stomach that is characterized by delayed gastric emptying in the absence of mechanical obstruction. The cause of gastroparesis is unknown, but it may be caused by a disruption of nerve signals to the intestine. The three most common etiologies are diabetes mellitus, idiopathic, and postsurgical. Other causes include medication, Parkinson's disease, collagen vascular disorders, thyroid dysfunction, liver disease, chronic renal insufficiency, and intestinal pseudo-obstruction. The prevalence of diabetic gastroparesis (DGP) appears to be higher in women than in men, for unknown reasons.

Diabetic gastroparesis affects about 40% of patients with type 1 diabetes and up to 30% of patients with type 2 diabetes and especially impacts those with long-standing disease. Both symptomatic and asymptomatic DGP seem to be associated with poor glycemic control by causing a mismatch between the action of insulin (or an oral hypoglycemic drug) and the absorption of nutrients. Treatment of gastroparesis depends on the severity of the symptoms.

SUMMARY

Disclosed herein is a gastrointestinal implant for use within a pylorus, a duodenal bulb, and a duodenum of a patient, the implant having an expanded configuration and a contracted configuration and comprising: a proximal portion comprising a hollow tubular braided structure of wire shaped to form a cylinder having a proximal end, a distal end, and a proximal wall extending radially inward from the proximal portion distal end, wherein the proximal wall has an outer circumference and an inner circumference and is configured with a first bias such that the inner circumference is located closer to the proximal portion proximal end than the proximal portion outer circumference; a neck portion comprising a cylinder having a proximal end and a distal end and extending distally from the inner circumference of the proximal portion, the neck portion having a length greater than a width of a pylorus; a distal portion comprising a hollow tubular braided structure of wire shaped to form a cylinder extending distally from the neck portion and having a proximal end, a distal end, and a distal wall extending radially inward from the distal portion proximal end, wherein the distal wall has an outer circumference and an inner circumference and is configured with a second bias such that the inner circumference is located closer to the distal portion distal end than the distal portion outer circumference; and a structural element coupled to the distal portion and configured to resist circumferential compression.

Also disclosed herein is a gastrointestinal device for implanting within a pylorus, a duodenal bulb, and a duodenum of a patient's gastrointestinal tract, the device having a central axis and comprising a first expandable portion comprising a hollow tubular braided structure of wire and having a first cylinder extending parallel to the central axis, the first cylinder having a proximal end, a distal end, and a length and a first face located at the distal end of the first cylinder and oriented transverse to the central axis; a neck portion extending from the first face of the first expandable portion parallel to the central axis, the neck portion having a first end, a second end, a wall extending between the first end and second end, and a diameter sized to fit within a pylorus; and a second expandable portion comprising a hollow tubular braided structure of wire and having a second cylinder extending parallel to the central axis, the second cylinder having a proximal end a distal end and a length and a second face located at the proximal end of the second cylinder and oriented transverse to the central axis wherein the length of the second cylinder is greater than one centimeter.

A gastrointestinal device for implanting within a pylorus, a duodenal bulb, and a duodenum of a patient's gastrointestinal tract, the device comprising a first expandable portion comprising a hollow tubular braided structure of wire shaped to include a disk portion configured to be located on a stomach side of the pylorus; a central cylinder portion having a first end, a second end, and a diameter that fits within the pylorus; a second expandable portion comprising a hollow tubular braided structure of wire shaped to include a cylinder having a proximal end, and distal end, a length between the proximal end and distal end, and a disk portion to be located on an intestinal side of the pylorus, the second expandable portion including a structural element configured to resist circumferential compression; and an intestinal bypass sleeve comprising a sleeve portion, wherein the sleeve portion extends from the duodenal bulb into the duodenum.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9 shows a pyloric implant from three points of view and illustrates an exemplary embodiment of a structural element according to some configurations.

FIG. 11 shows a pyloric implant from three points of view and illustrates an exemplary embodiment of a structural element according to some configurations.

FIG. 12 shows an exemplary embodiment of a structural element and a pyloric implant with a structural element attached, according to some configurations.

FIG. 13 shows an exemplary embodiment of a structural element and a pyloric implant with a structural element attached, according to some configurations.

FIG. 14 shows an exemplary embodiment of a structural element and a pyloric implant with a structural element attached, according to some configurations.

FIG. 16 shows an exemplary embodiment of a structural element and various views of a pyloric implant with a structural element attached, according to some configurations.

FIG. 19 shows an exemplary embodiment of a structural element and various views of a pyloric implant with a structural element attached, according to some configurations.

FIG. 20 shows an exemplary embodiment of a structural element and various views of a pyloric implant with a structural element attached, according to some configurations.

FIG. 21 shows an exemplary embodiment of a structural element and various views of a pyloric implant with various structural elements attached, according to some configurations.

FIG. 22 shows an exemplary embodiment of a structural element and various views of a pyloric implant with a structural element attached, according to some configurations.

FIG. 23 shows an exemplary embodiment of a structural element and various views of a pyloric implant with a structural element attached, according to some configurations.

FIG. 24 shows an exemplary embodiment of a structural element and various views of a pyloric implant with a structural element attached, according to some configurations.

DETAILED DESCRIPTION OF THE DRAWINGS

According to some embodiments, the present disclosure includes an apparatus and method to place and/or anchor a gastrointestinal device within the pyloric antrum, pylorus, duodenum and jejunum. The gastrointestinal device disclosed herein may be implanted by inserting it endoscopically (when the device is loaded into a delivery catheter) through the mouth, throat, stomach and intestines. The gastrointestinal device may include an anchor that can be implanted and remain within a pylorus. The gastrointestinal device may also include an expandable anchor having a flexible thin-walled sleeve attached to the distal end of the anchor. In some embodiments, secondary anchors may also anchor other portions of the thin-walled sleeve.

The instant disclosure may include an expandable anchor that can also be used to hold open the pylorus and may help to reduce the symptoms of gastroparesis by allowing the stomach contents to exit the stomach easier through the pylorus into the duodenum. The instant disclosure may include additional structure, such as an expandable anchor having a short bypass sleeve or no bypass sleeve. In some embodiments, an active pumping means may also be attached to the expandable anchor to actively pump the stomach contents from the pyloric antrum into the duodenum.

The present disclosure is an exemplary version of the apparatus and methods described in U.S. Pat. No. 9,044,300, entitled "Gastrointestinal Prostheses," granted Jun. 2, 2015, which is incorporated herein by reference. The instant disclosure provides improvements on the performance of previously designed implants. Certain design improvements are generally intended to improve the anchoring performance of the implant and decrease the likelihood that the implant can migrate in response to physiological changes of the body. Additional improvements disclosed herein minimize the likelihood that the sleeve portion of the implant becomes everted or obstructed.

Figure 1:
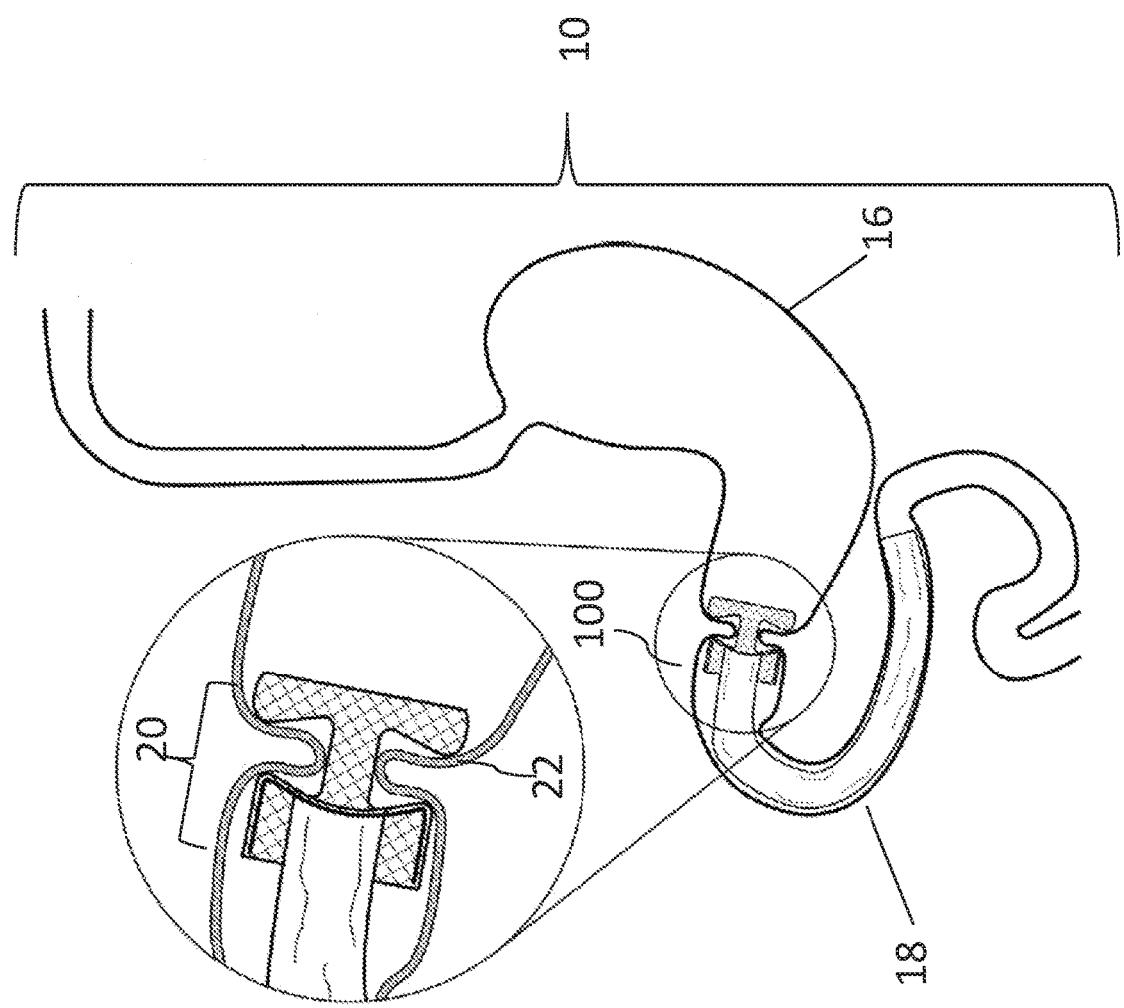
FIG. 1 is a cross-sectional view of a portion of the digestive tract in a human body with a pyloric anchor and sleeve implanted in the pylorus.

FIG. 1 is a cross-sectional view of a portion of a human digestive track 10, showing an embodiment of a device 100 that may be implanted between the stomach 16 and the small intestine 18. As shown in FIG. 1, the device 100 may be implanted generally within the pylorus 20 with at least a section configured to remain within the pyloric antrum 22. The device 100 may be configured to be implanted with portions of the device 100 held within the stomach 16, the pylorus 20, and the small intestine 18. The device 100 may be endoscopically implanted within the pylorus 20 in a compressed configuration. After implantation, the device 100 may be released and assume an expanded configuration. Once in the expanded configuration, the device 100 generally anchors itself to remain with at least a portion of the device 100 within the pylorus 20.

Figure 2:
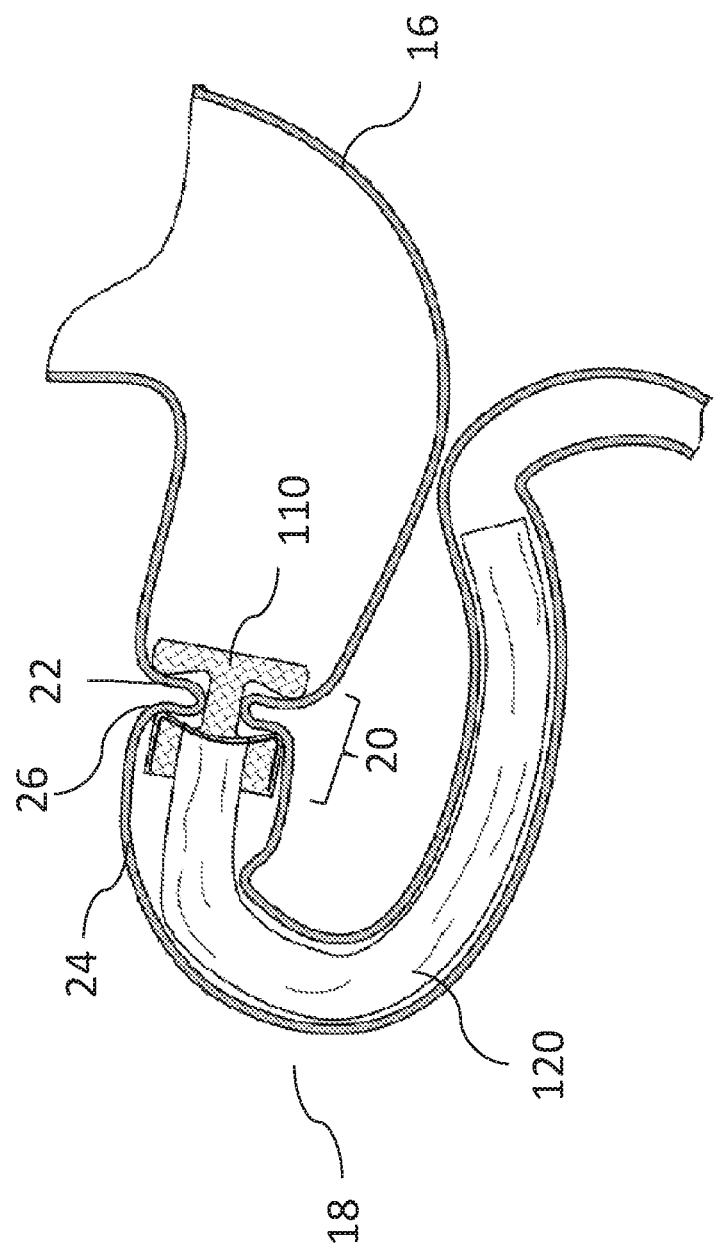
FIG. 2 is a cross-sectional view of a portion of the digestive tract in a human body with a pyloric anchor implanted and an intestinal bypass sleeve attached.

FIG. 2 is a cross-sectional view of a portion of the digestive tract in a human body showing the pyloric antrum 22, pylorus 20, duodenum 24, and duodenal bulb 26. FIG. 2 also shows the device 100 implanted between the stomach 16 and small intestine 18. As shown in FIG. 2, the device 100 may generally comprise an expandable portion 110 that holds or anchors the device 100 in place, and a sleeve portion 120.

The device 100 as a whole may be alternatively referred to as an implant, an implantable device, a gastrointestinal device, a gastrointestinal implant, or a pyloric implant. The portion of the device 100 that is able to expand and hold the device 100 in place after implantation may be referred to as the anchor, the anchoring portion, the holder, or the holding portion. The sleeve 120 portion of the device 100 that is shown within the small intestine 18 may be alternatively referred to as the sleeve, the intestinal sleeve, the bypass sleeve, the intestinal bypass sleeve, the liner, or the bypass liner. For example, the device 100 may include an intestinal bypass sleeve 120 that is designed to be implanted in the duodenum 26 from the pylorus 20 to the ligament of treitz (not shown). As shown in FIG. 2, the sleeve 120 is generally held in place in the small intestine 18 by the anchoring portion 110 of the device that anchors within or on the pylorus 20.

According to various embodiments, the sleeve 120, the anchor 110, or both are further coupled at or within the pylorus 20 using one or more of the techniques described in either of U.S. Pat. Nos. 8,211,186 or 8,282,598 filed Jul. 9, 2010, entitled "External Anchoring Configuration for Modular Gastrointestinal Prostheses," both of which are incorporated herein by reference. According to various embodiments of the invention, the sleeve 120 may be configured to be coupled to the anchor 110, using one or more of the configurations disclosed in U.S. Pat. No. 8,702,641, filed Jan. 7, 2011, entitled "Gastrointestinal Prostheses Having Partial Bypass Configurations," which is incorporated herein by reference.

Figure 3:
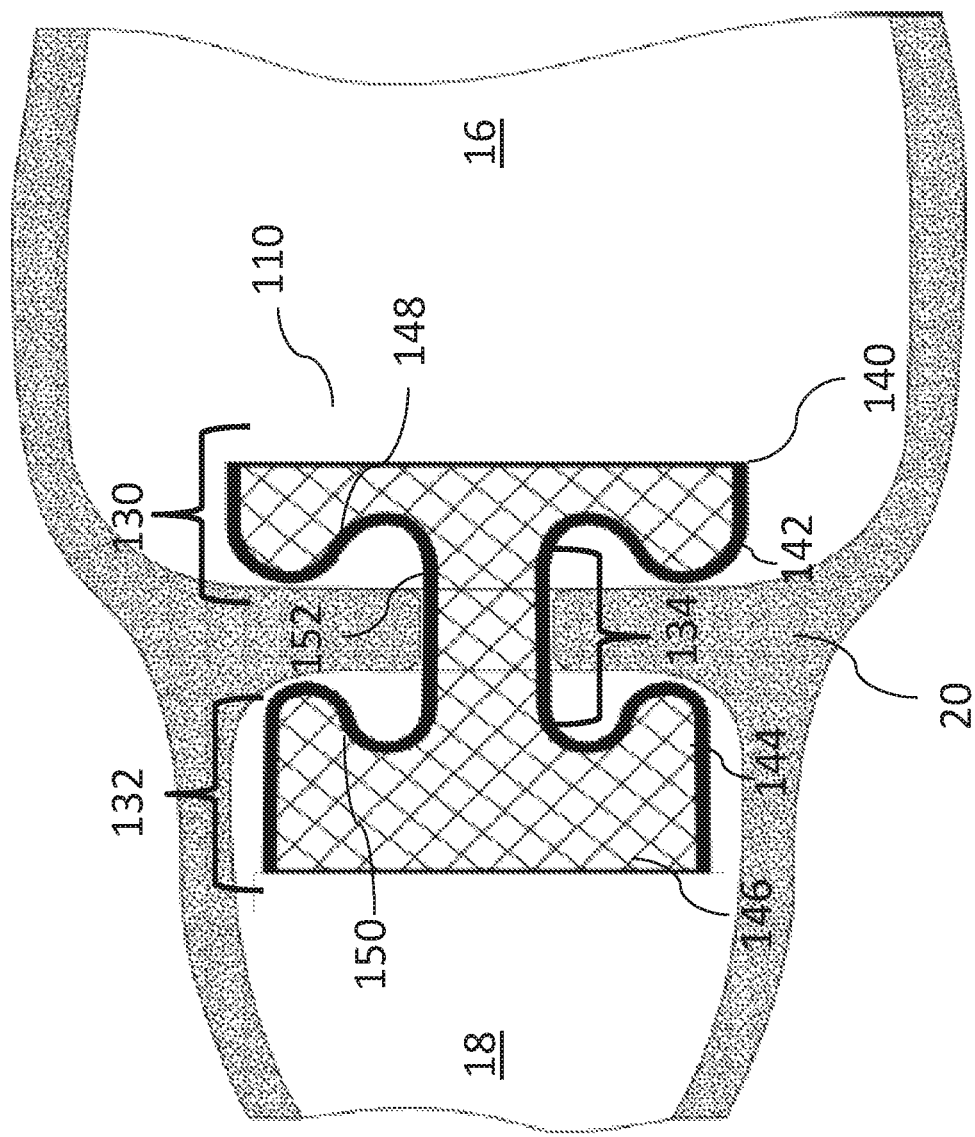
FIG. 3 is a cross-sectional view of a portion of the digestive tract in a human body with a pyloric anchor implanted in the pylorus, showing a braided wire structure of the anchor according to some embodiments.

FIG. 3 illustrates an exemplary embodiment of the anchor 110. The anchor 110 has an overall cylindrical shape with a length and a width. In some embodiments, the anchor 110 has an overall cylindrical shape, with a central axis oriented along a longitudinal direction. The anchor 110 has a proximal portion 130, a distal portion 132, and a neck portion 134.

In some embodiments, the proximal portion 130 is shaped in a circular or disk shape. In some embodiments, the proximal portion 130 is shaped in a circular or disk shape having a lip or rim. The proximal portion 130 may interchangeably be referred to as a proximal flange. The lip or rim may define a proximal portion proximal end 140 and a proximal portion distal end 142. The lip or rim forming the proximal portion proximal end 140 and the proximal portion distal end 142 may define an overall cylindrical or tubular shape. In some embodiments, the proximal portion 130 circular or disk shape defines a face or wall 148 also referred to herein as the proximal portion wall 148 or proximal flange wall. The proximal flange wall 148 may be a disk that is located on the distal side 142 of the proximal flange 130. The proximal flange wall 148 may be a disk or disk shaped and oriented transverse to the central axis. In general, the proximal end 140 of the proximal portion 130 is open to allow chyme to enter. The distal end 142 of the proximal portion 130 may be connected to the proximal flange wall 148.

In some embodiments, the neck portion 134 defines a through-lumen 152 that allows chyme to flow from the stomach 16 to the small intestine 18. The neck portion 134 may be rigid to hold the pylorus 20 open or it may be compliant to allow the opening and closure of the through lumen 152 with the pylorus 20.

In some embodiments, the distal portion 132 is shaped in a circular or tubular shape. In some embodiments, the distal portion 132 is shaped in a circular, disk, or tubular shape having a lip or rim. The distal portion 132 may interchangeably be referred to as a distal flange. The lip or rim may define a distal portion proximal end 144 and a distal portion distal end 146. The lip or rim forming the distal portion proximal end 144 and the distal portion distal end 146 may define an overall cylindrical or tubular shape. In some embodiments, the distal portion 132 circular or disk shape defines a face or wall 150 also referred to herein as the distal portion wall 150 or distal flange wall. The distal flange wall 150 may be located on the proximal side of the distal flange 132. The distal flange wall 150 may be formed as a disk or disk shaped that is oriented transverse to the central axis. The proximal end 144 of the distal portion 132 may be connected to the distal flange wall 150. In general, the distal portion 132 or distal flange is located in the duodenum and the distal flange 132 has an opening at the distal end 146 that faces the intestine 18.

In some embodiments, the distal flange 132, and the neck portion 134 each form a generally cylindrical shape, each with an independent diameter. For example, the proximal flange 130 has an overall cylindrical shape with an open proximal end 140 having a first diameter, and a distal end 142 having a proximal flange wall 148 that necks down to a diameter of the neck portion 134. The proximal flange wall 148 can be shaped having an angle with a bias in relation to the central axis. The neck portion 134 comprises a cylinder having a second diameter and extends between the proximal flange 130 and the distal flange 132. The distal flange 132 has a generally cylindrical shape and includes the distal flange wall 150 starting from the neck portion 134 and expanding radially from the central axis. The distal flange 132 has a proximal end 144 that is positioned near the pylorus 20, and a distal end 146 that faces into the small intestine 18. The anchor can be oriented by a central axis that is defined as the direction traveling from the proximal flange 130, through the neck portion 134, and continuing through the distal flange 132.

The braided wire structure of the implant may be formed into a shape to promote anchoring to the tissue of a patient. For example, the proximal flange wall 148 and distal flange wall 150 can be angled in relation to the neck portion 134 in order to provide certain spatial relationships to the pylorus 20 at particular locations. In some embodiments, both the proximal flange 130 and distal flange 132 are shaped to apply force F to the proximal and distal face of the pylorus 20, respectively. The effect of this force is intended to keep the implant in place, anchored across the pylorus 20.

The overall length of the anchor 110 can be from about 10.0 mm to about 100.0 mm, but varying sized anchors may be formed, depending on a patient's anatomy or anatomical fit. In some embodiments, the anchor 110 length may be from about 10.0 mm to about 100 mm, from about 25.0 mm to about 75.0 mm, from about 40.0 mm to about 60.0 mm, or any length within these ranges. An exemplary anchor 110 has been formed that is about 50.0 mm long but typical anchors may be in the range of between about 45.0 mm and 55.0 mm. In some embodiments, the diameter of the proximal flange 130 can be from about 10.0 mm to about 75.0 mm, or any range in between, for example from about 25.0 mm to about 60.0 mm, and from about 40.0 mm to about 55.0 mm. An exemplary anchor 110 has been formed with the diameter of the proximal flange 130 about 40.0 mm.

In some embodiments, the distal flange 132 is shaped as a cylinder with a generally open distal end 146 and partially restricted proximal end 144 connected to the distal flange wall 150. The distal flange 132 may be formed in an overall cylindrical shape having a diameter. The length and diameter of the distal flange 132 can be sized to prevent canting or tilting within a tubular anatomical structure such as the duodenum. In some embodiments, the diameter of the distal flange 132 may be from about 5.00 mm to about 60.0 mm, or any range in between, for example from about 20.0 mm to about 50.0 mm, or from about 30.0 mm to about 40.0 mm. For example, the distal flange can have a length of roughly 18.0 mm and a diameter of 35.0 mm, to ensure the structure can remain positioned within a tubular anatomic structure such as the duodenal bulb with a diameter of about 40.0 mm. An exemplary anchor 110 has been formed with the diameter of the distal flange 132 about 35.0 mm in diameter.

As shown in FIG. 3, in some embodiments, the diameter of the distal flange 132 may define a gap or space between the diameter of the distal flange 132 and the duodenum. In some embodiments, a gap or space between the diameter of the distal flange 132 and the duodenum may allow the anchor 110 to rotate or turn in a direction generally perpendicular to the central axis of the anchor 110 or a longitudinal axis defined by the center of the opening of the pylorus. If the anchor 110 is allowed to rotate after it is implanted in a patient, the distal flange 132 or anchor 110 or both may undergo unwanted movement or deflection and in some cases become dislodged. Rotation or turning of the anchor 110 or the distal flange 132 may be inhibited by providing a distal flange 132 having a suitable length and diameter. A distal flange 132 length may allow the distal flange 132 to contact the duodenum and prevent further rotation before the distal flange 132 or anchor 110 become deflected or dislodged. The length of the distal flange 132 may determine the degree of rotation the anchor 110 may undergo before contacting the duodenum. In some embodiments, the length and the diameter of the distal flange 132 are sized such that upon rotation or canting of the anchor 110 away from the longitudinal axis, the distal end 146 of the distal flange 132 will make contact with the intestinal wall and therefore will resist migration of the anchor 110 within a patient. It has been found that a suitable distal flange 132 length that may inhibit unwanted rotation or canting or longitudinal deflection may be from about 10.0 mm to about 50.0 mm or any length in between. In some embodiments, the distal flange 132 may have a length that is sized in relation to the width of the distal flange 132.

In some embodiments, the distal flange 132 may have a length that is sized in relation to the length of the proximal flange 130. For example, the length of the distal flange 132 may be the same length as the proximal flange 130. In some embodiments, the length of the distal flange 132 may be multiples of the length of the proximal flange 130. For example, the distal flange 132 may be one and a half, two times, three times, or greater, the length of the proximal flange 130.

In some embodiments, the diameter of the neck portion 134 may be from about 2.0 mm to about 30.0 mm, or any range in between. for example from about 5.00 mm to about 30.0 mm, and from about 10.0 mm to about 20.0 mm. An exemplary anchor 110 has been formed with the diameter of the neck portion 134 about 15.0 mm.

In some embodiments, the length of the neck portion 134 may be approximately the width of a patient's pylorus. In some embodiments, the length of the neck portion 134 may be longer than the width of a patient's pylorus to provide a gap between the proximal flange wall 148 and the distal flange wall 150 and the pylorus 20. In some embodiments, the neck portion 134 may be sized to allow the proximal flange wall 148 and the distal flange wall 150 to contact the pylorus 20. In some embodiments, the anchor 110 is compressible in diameter and the overall diameter can be reduced to about 5.00 to 10.0 mm in diameter typically to allow the anchor 110 to be loaded into a catheter (described further below).

Figure 4:
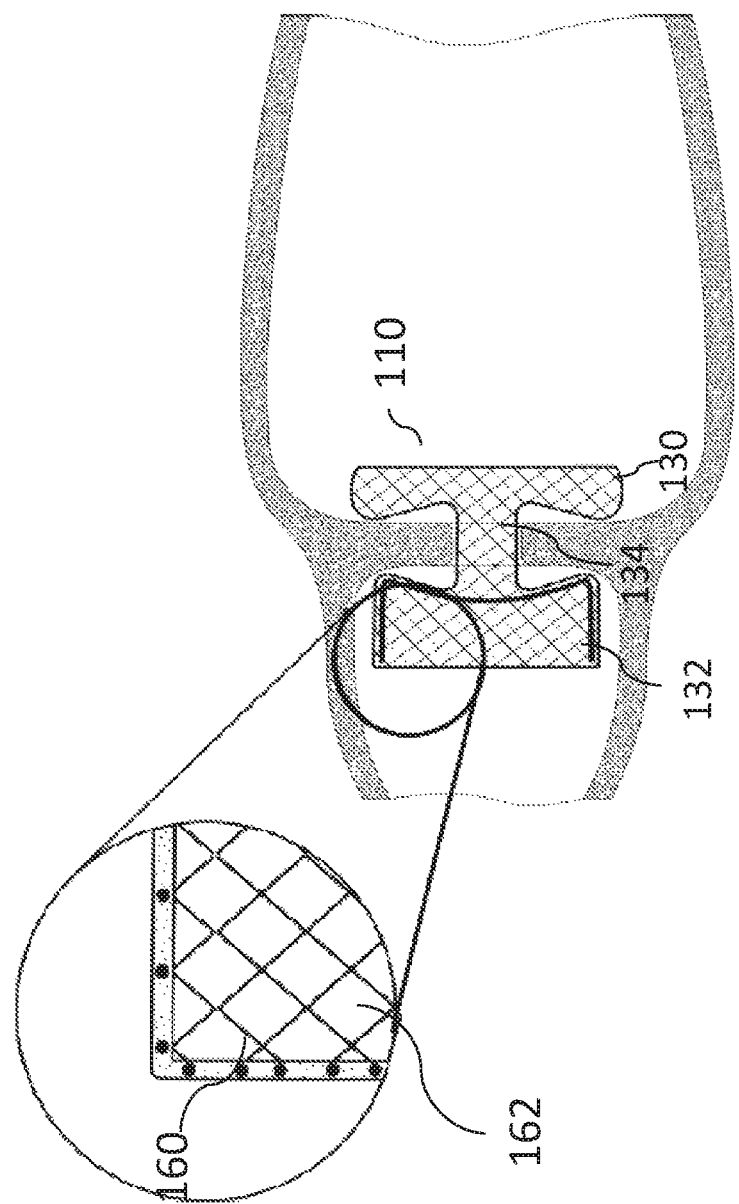
FIG. 4 is a cross-sectional view of a portion of the digestive tract in a human body with a pyloric anchor implanted in the pylorus, showing an overall structure of the anchor and flanges according to some embodiments.

As shown in FIG. 4, in some embodiments, the anchor 110 is formed from a hollow tubular braided structure 160 of wire. The diameter of the wire that is used to form the braided structure 160 can range from about 0.001 inch to about 0.014 inch, from about 0.004 inch to about 0.011 inch, from about 0.006 inch to about 0.009 or any diameter within this range such as 0.008 inch The braided structure 160 of wire is weaved to form a mesh structure 162. The mesh structure 162 may be shaped to form the various elements of the anchor 110. The mesh structure 162 is formed into a shape with a proximal flange 130, a neck portion 134, and a distal flange 132.

The braided structure may be weaved to form a mesh structure 162, and the mesh can be formed into various components. For example, the mesh structure 162 may be formed into disks or cylinders of the various parts of the anchor 110. Suitably sized cylinders may be formed from the mesh structure and may have a diameter from about 10 mm in diameter to about 70 mm in diameter, from about 14 mm to about 50 mm in diameter, and any diameter in between. In some embodiments, a braided structure 160 of different diameters may be used at various locations of the anchor 110. For example, an anchor 110 may be created using a braided structure 160 having a diameter of about 14 mm for the neck portion 134, a braided structure 160 having a diameter of about 34 mm for the distal flange 132, and a braided structure 160 having a diameter of about 40 mm for the proximal flange 130. In exemplary embodiments, the number of wire ends in the braided structure 160 is 96 ends, but it can range from 4 ends to 256 ends. The wire can be formed from a metal such as Nitinol, MP35N, L605, Elgiloy, stainless steel or from a plastic such as Pet, Peek or Delrin or other suitable material.

The anchor 110 can be covered on the outside and/or inside side with a polymer membrane covering. The membrane covering the anchor 110 may be made from a thin-walled polymer material such as silicone, polyurethane, polytetrafluoroethylene, fluorinated ethylene propylene, polyethylene, expanded poly tetrafluoroethylene (ePTFE) or other suitable material. In some embodiments, the wall thickness of the membrane covering the anchor 110 may be in the range of 0.001 inch to 0.030 inch thick. The membrane may be made by extrusion, dip coating from a liquid solution, powder coated from fine particles of polymer or paste extruded and then stretched as is the case with ePTFE. The anchor membrane may also be cut from a flat sheet of material such as ePTFE and then bonded or sewn into a disk shape or spherical shaped structure and then attached to the anchor 110 by sewing or gluing with a polymer such as FEP.

In some embodiments, the anchor 110 also incorporates a structural element contained within the overall structure. Various configurations of the structural element can be found in the following FIGS. 5 through 24.

Figure 5:
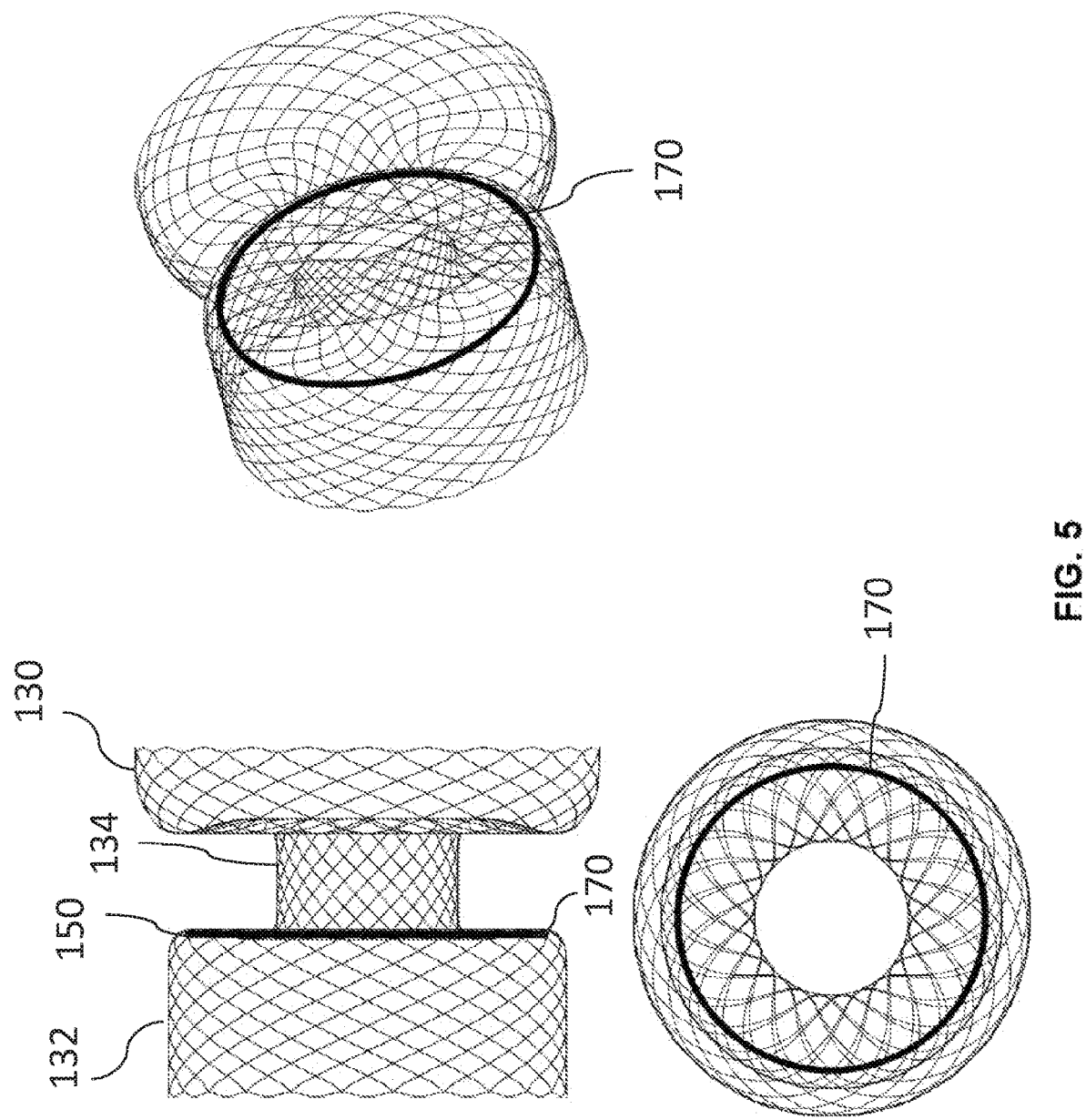
FIG. 5 shows a pyloric implant from three points of view and illustrates an exemplary embodiment of a structural element having a ring configuration.

FIG. 5 shows three views of the implant described in FIG. 3 and is intended to highlight an exemplary embodiment of an anchor 110 and a structural element 170. In some embodiments, a structural element 170 is located in any of the proximal flange 130, the distal flange 132, or both. In an exemplary embodiment, a structural element 170 is located at least within the distal flange 132. For example, a structural element 170 may be located in the distal flange 132, proximate the neck portion 134, and may be weaved through the mesh structure 162 to maintain a suitable position. The structural element 170 is typically designed to provide support to the braided structure and contribute to resisting compression or deformation of the overall shape of the anchor 110. The braided structure 160 alone will compress uniformly in response to a circumferential force and therefore the body may be able to push the implant from its location across the pylorus, leading to migration. With the structural element 170 in place, the implant is more resistant to compression due to the shape and resistance of the structural element 170. The structural element 170 may deform independently from the braided structure 160 and therefore may provide support in addition to resistance to compression. The structural element 170 may provide support to the overall length, shape, diameter, or bias of the anchor 110.

The structural element 170 can be made from a metal such as Nitinol, MP35N, L605, Elgiloy, stainless steel or from a plastic such as PET, PEEK, or Delrin or other suitable material. In a preferred embodiment, the structural element 170 is made from superelastic Nitinol wire formed into the particular shape. The wire has a diameter from about 0.010 inch to about 0.030 inch, or from about 0.015 inch to about 0.025 inch, or any diameter in between. In one example, a structural element was formed from Nitinol wire having a diameter of about 0.020 inch in diameter. If a structural element having a particular rigidity or stiffness is required, often the size and material that the stiffening element is made from can be used to control these properties. As an example, Nitinol wire has been used to form stiffening elements, which have a compressive and expansive strength that is a function of the diameter of the wire used to make the stiffening element.

In some embodiments, the various components of the anchor 110, including the braided structure 160, the mesh structure 162, the mesh structure with a membrane, and the structural element 170 provide structural support both individually and in combination. The braided structure 160 and mesh structure 162 may contribute support both in a radial and longitudinal direction. The structural element 170 may enhance the overall strength and rigidity of the anchor both in the radial and longitudinal direction. Additionally, the structural element 170 may be tailored to provide a bias to the braided structure 160 and mesh structure 162 to allow the anchor to form a particular shape in response to certain forces. For example, the structural element 170 may add stiffness to the anchor 110 and allow it to maintain an effective circumference. The structural element 170 may provide a compression limit to the anchor 110. The structural element 170 may add longitudinal stability. The structural element 170 may inhibit the anchor 110 from moving through the pylorus.

As shown in FIG. 5, in some embodiments, the structural element 170 is comprised in the shape of a ring. The diameter of a ring formed to create a structural element may be sized to form a suitable fit for use in an anchor 110, or at various locations on an anchor. For example, the diameter of a ring may be from about 20 mm to about 50 mm, from about 25 mm to about 45 mm, from about 30 mm to about 40 mm, and any diameter within this range. In one example, a ring was formed having a diameter of about 35 mm.

Figure 6:
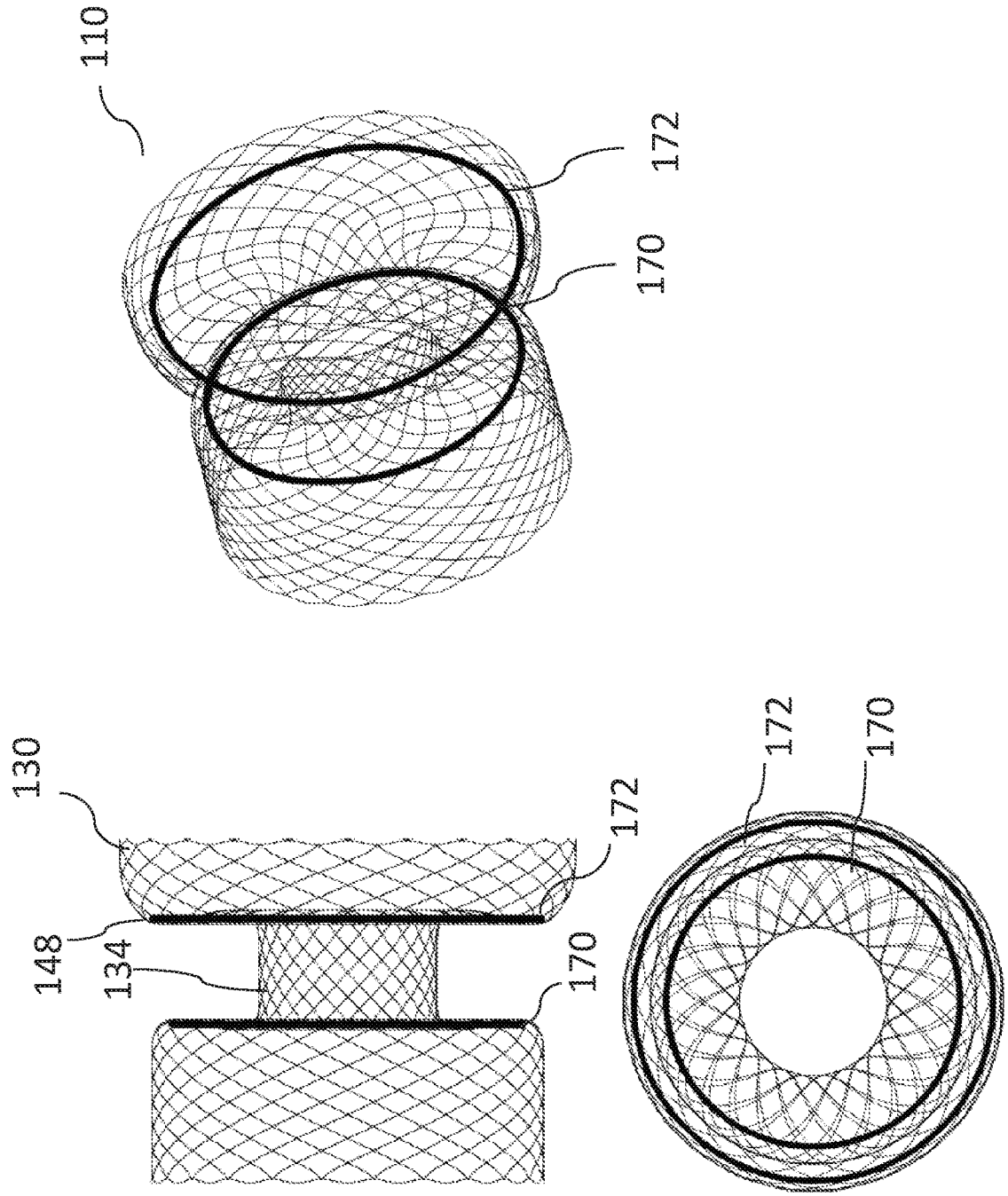
FIG. 6 shows a pyloric implant from three points of view and illustrates an exemplary embodiment having multiple structural elements having a ring configuration.

FIG. 6 describes an alternative embodiment to the implant shown in FIG. 5. In some embodiment, the anchor 110 incorporates a proximal structural element 172. The proximal structural element 172 is located at the proximal wall or face 148 of the proximal flange 130, nearest to the neck portion 134 of the anchor 110. The function of the proximal structural element 172 is to resist compression of the overall structure. The proximal structural element 172 is weaved through the mesh structure 162 to secure it to the anchor 110. The proximal structural 172 element may be made from the same material as the structural element 170.

Figure 7:
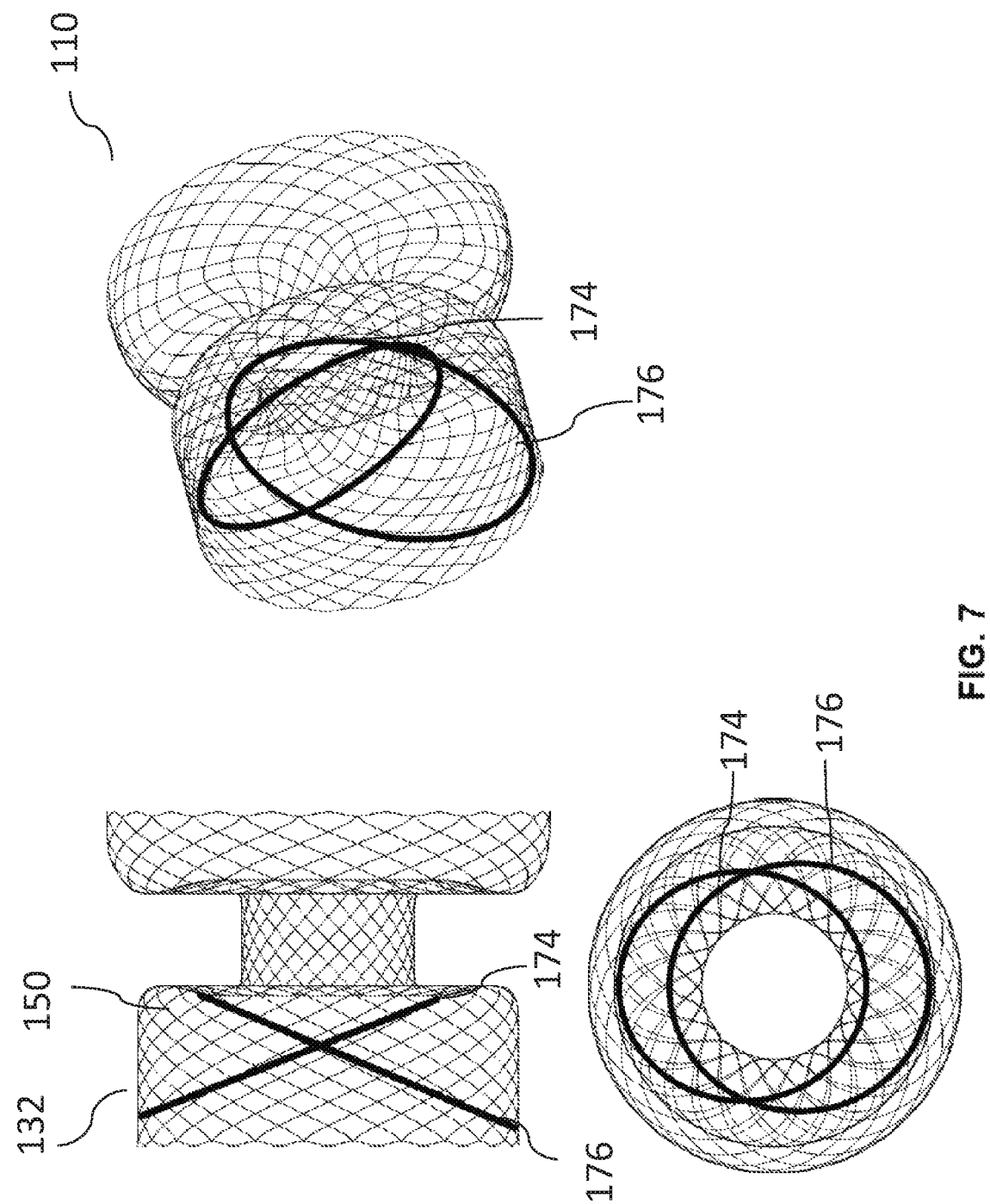
FIG. 7 shows a pyloric implant from three points of view and illustrates an exemplary embodiment having multiple structural elements having a ring configuration.

FIG. 7 is an alternative embodiment to the implant shown in FIG. 5. The anchor 110 incorporates two structural elements 174, 176 each of which are 180 degrees apart, orientated out-of-plane relative to the distal wall or face 150 of the distal flange 132. This configuration provides an additional option not available in the design shown in FIG. 5 by enabling the structure to be collapsed into a shape that can be loaded into a small diameter tube for the purpose of delivering or retrieving the implant endoscopically in a human. While the structural elements 174, 176 can still resist circumferential compression, when the structure is pulled into a tube, the structural elements 174, 176 will collapse into an elliptical shape. The structural elements 174, 176 included here comprise rings.

Figure 8:
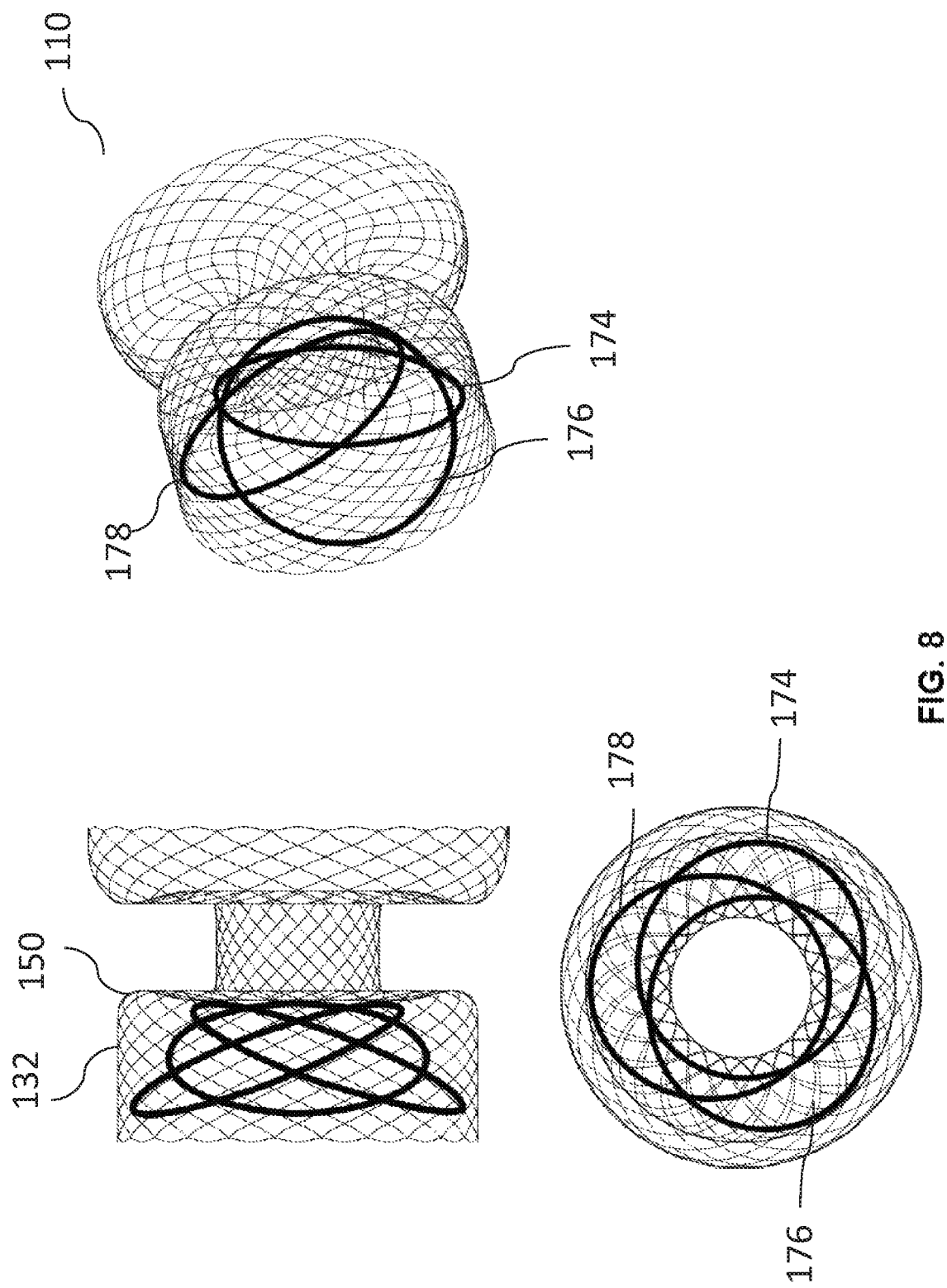
FIG. 8 shows a pyloric implant from three points of view and illustrates an exemplary embodiment having multiple structural elements having a ring configuration.

FIG. 8 is an additional embodiment to the implant shown in FIG. 7 in which the anchor 110 incorporates three structural elements 174, 176, 178. In this example, the structural elements 174, 176, 178 comprise rings each 120 degrees apart from each of the others, orientated out-of-plane relative to the wall or face 150 of the distal flange 132. This configuration provides an advantage over the design shown in FIG. 7 because it is symmetrical with respect to the distal flange 132 and with respect to a patient's anatomy. The overall structure can still be collapsed into a shape that can be loaded into a small diameter tube for the purpose of delivering or retrieving the implant endoscopically in a human.

FIG. 9 illustrates an additional embodiment of an alternative structural element 190. The anchor 110 incorporates a single alternative structural element 190 shaped to provide additional strength to the overall structure. This configuration provides an advantage over certain embodiments by enabling the structure to be collapsed more easily into a shape that can be loaded into a small diameter tube for the purpose of delivering or retrieving the implant endoscopically in a human. While the alternative structural element 190 can still resist circumferential compression, when the structure is pulled into a tube, the alternative structural element 190 will collapse into an elliptical shape. Various structural features also enable the anchor 110 containing an alternative structural element 190 to be collapsed and provide a bias to the direction of collapse.

Figure 10:
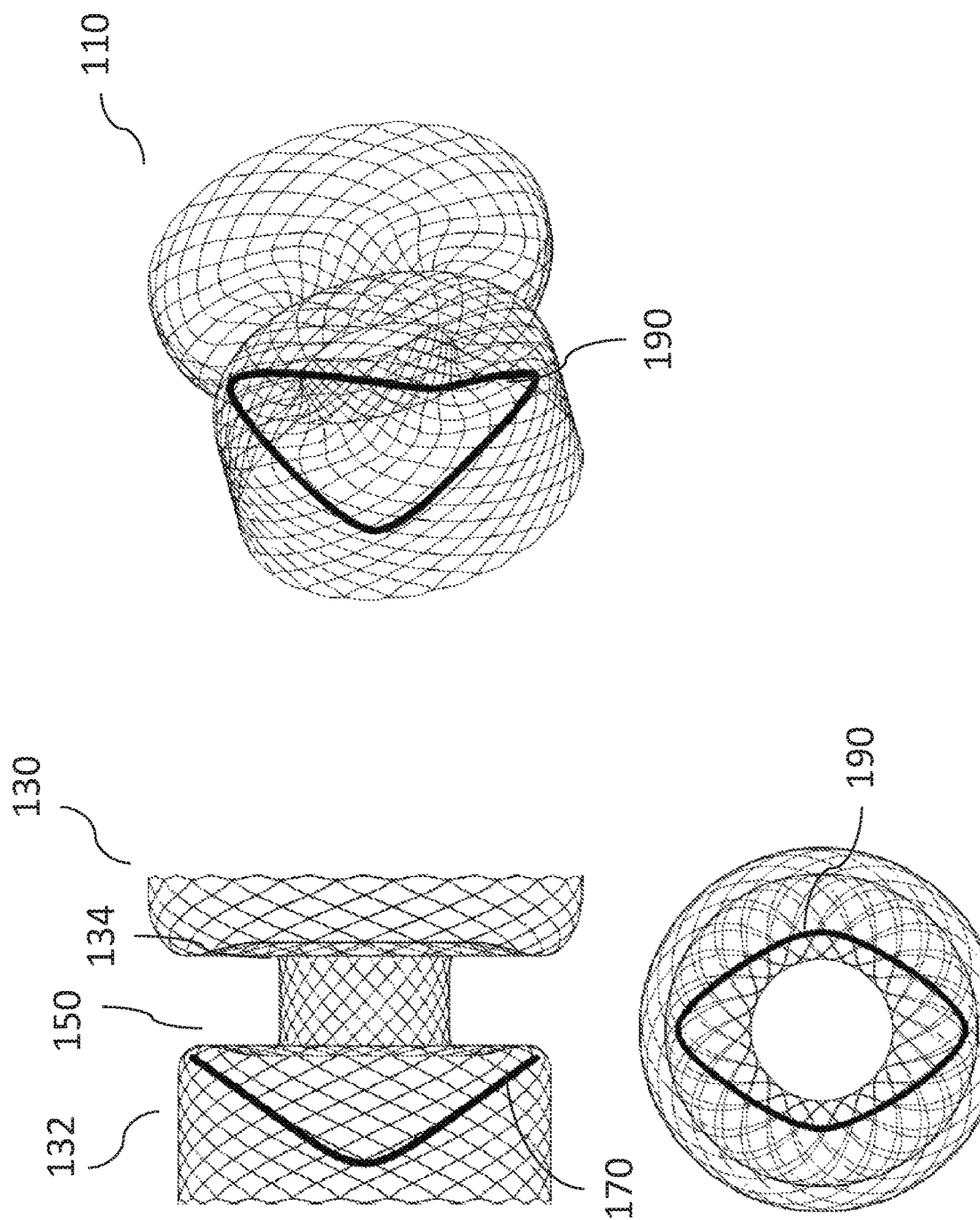
FIG. 10 shows a pyloric implant from three points of view and illustrates an exemplary embodiment of a structural element according to some configurations.
Figure 15:
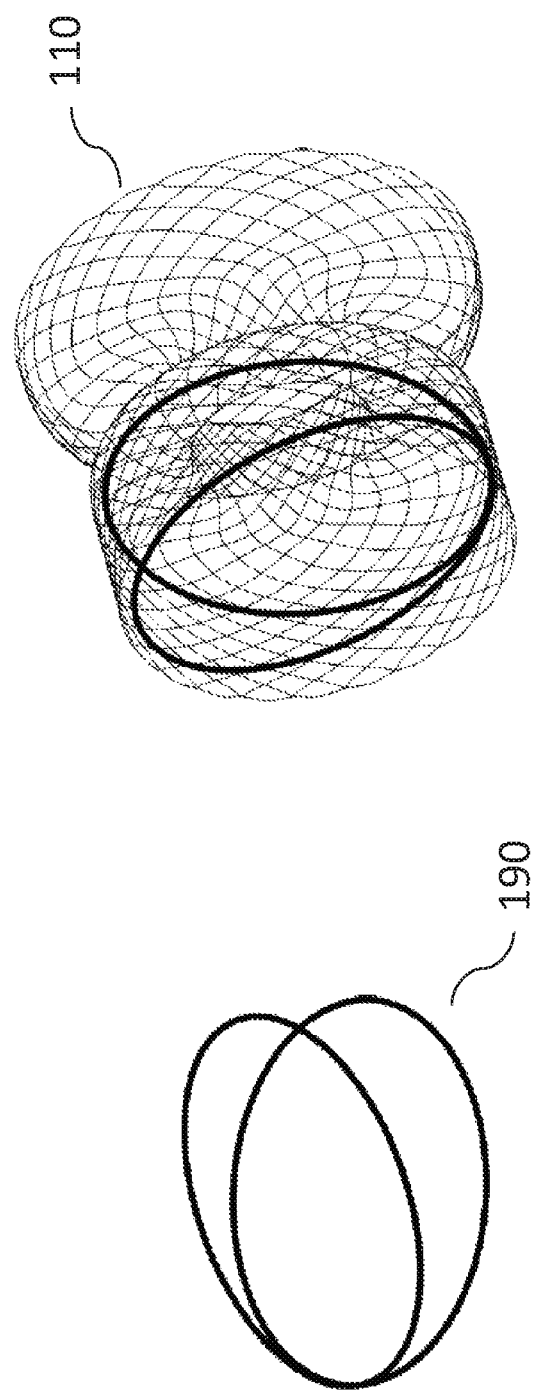
FIG. 15 shows an exemplary embodiment of a structural element having rings and a pyloric implant with a structural element attached, according to some configurations.
Figure 17:
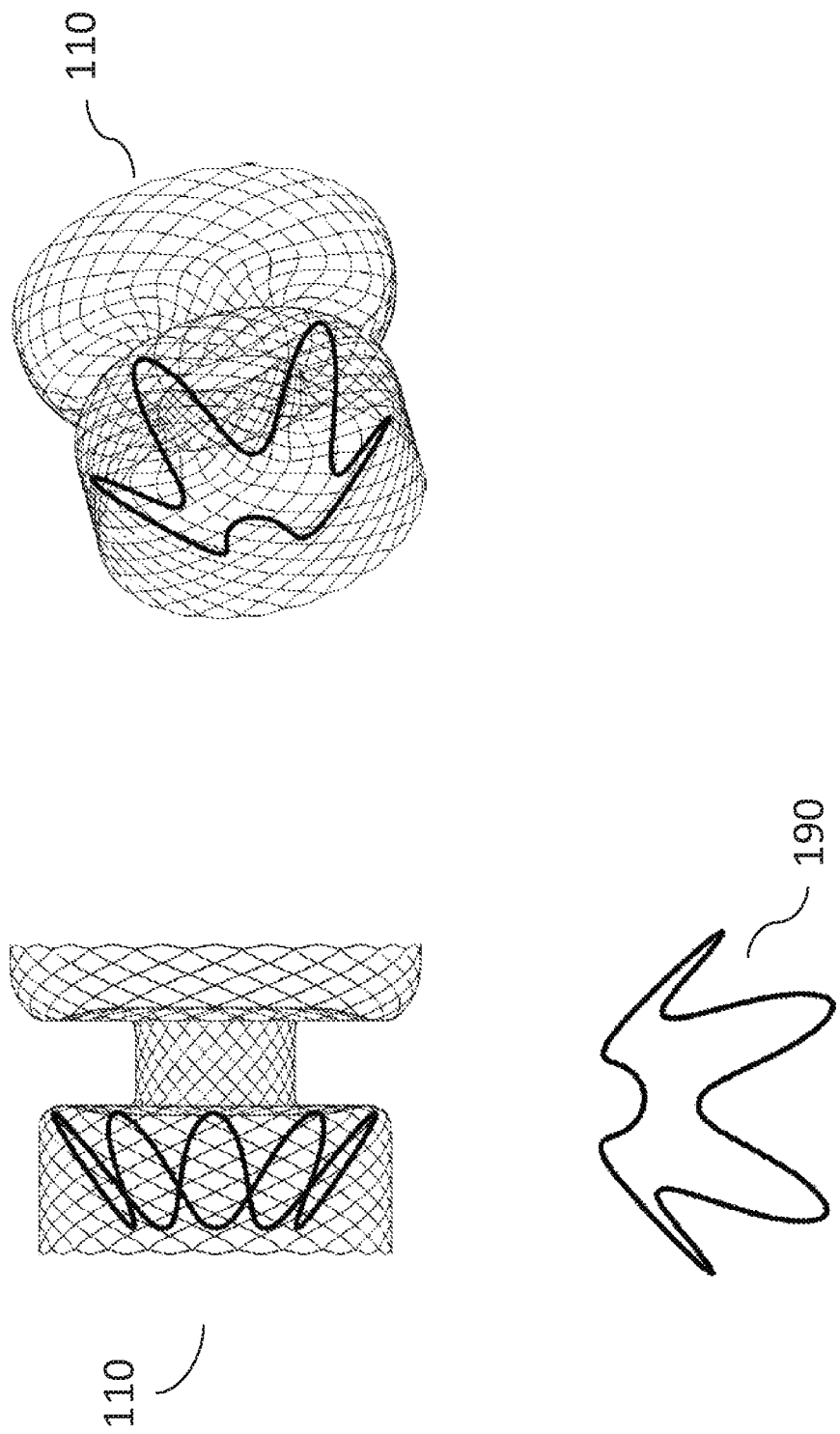
FIG. 17 shows an exemplary embodiment of a structural element and various views of a pyloric implant with a structural element attached, according to some configurations.
Figure 18:
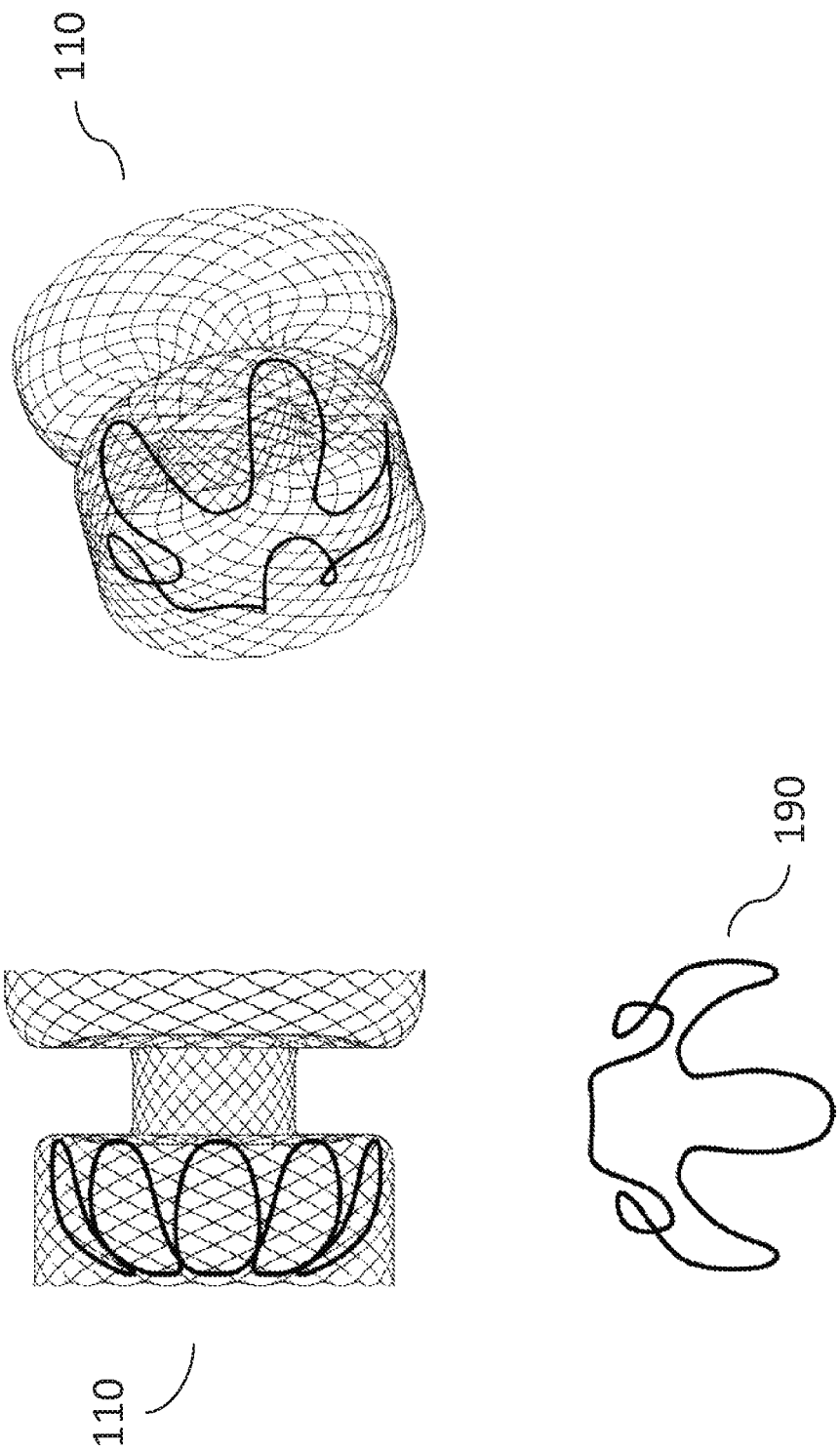
FIG. 18 shows an exemplary embodiment of a structural element and various views of a pyloric implant with a structural element attached, according to some configurations.

FIG. 10 illustrates an additional embodiment of an alternative structural element 190. The anchor 110 incorporates an alternative structural element 190 shaped to provide additional strength to the overall implant structure. This configuration enables the structure to be collapsed into a shape that can be loaded into a small diameter tube for the purpose of delivering or retrieving the implant endoscopically in a human. While the alternative structural element 190 can still resist circumferential compression, when the structure is pulled into a tube, the alternative structural element 190 will collapse into an elliptical shape. Various structural features also enable the anchor 110 containing an alternative structural element 190 to be collapsed and provide a bias to the direction of collapse.

FIGS. 11 to 20 illustrate various embodiments and shapes of an alternative structural element 190. The embodiments shown in FIGS. 11 to 20 all have the features of providing additional strength to the overall structure of the anchor 110 and are collapsible. The illustrated embodiments enable the anchor 110 to be collapsed into a shape that can be loaded into a small diameter tube for the purpose of delivering or retrieving the implant endoscopically in a human. Various structural features also enable the anchor 110 containing an alternative structural element 190 to be collapsed and provide a bias to the direction of collapse.

The anchor 110 illustrated in FIGS. 9 to 24 has the advantage that a structural element 190 has been added to provide structural support to the anchor 110 in addition to the braided structure 160. To provide structural support and to optimize the expanded configuration of either the proximal 130 flange, the distal flange 132, or both flanges, the orientation of the structural element 190 is arranged to provide any of a static radial force, a static longitudinal force, or both. As an example, FIG. 13 contains an embodiment of a structural element 190 that is capable of providing both radial support and longitudinal support. As used herein, the term longitudinal support refers to structural support for maintaining the anchor 110 in an expanded configuration along a direction parallel to the central axis. As used herein, the term radial support refers to support for maintaining the anchor 110 in an expanded configuration along a direction perpendicular to the central axis. Often this can be accomplished by having the structural element 190 connected to the neck portion of the anchor 110 and transverse a flange in a radial direction.

In the structure illustrated in FIG. 13, the structural element 190 is generally attached to the anchor 110 at various touch points. The shape and size of the structural element 190 can be chosen to provide a suitable fit for a particular patient. It may be that certain portions of an anchor 110 require greater longitudinal support. This can be accomplished by increasing the size of the structural element 190 in the longitudinal direction, as illustrated by comparing the structural element 190 in FIGS. 11 to 13. For example, in certain embodiments, a patient may need greater support in the longitudinal direction which can be accomplished by providing a compressive force by the anchor 110 in the longitudinal direction. Another option is to provide structural support in the longitudinal direction past the end of the distal flange. This may be accomplished by using the embodiment illustrated in FIG. 13.

In some embodiments, the structural element 190 illustrated in FIG. 13 may be used, for example, to maintain a sleeve that is attached to the anchor 110 in an open configuration. As an example, a sleeve may be attached to the neck portion of the anchor 110 at the distal wall. The sleeve may be attached to the structural element 190 at various points along the sleeve as the sleeve extends through the end of the distal flange and continues out in a longitudinal direction. The structural element 190 is sized to extend past the end of the distal flange and thus a portion of the structural element 190 can be attached to the sleeve outside the distal flange. In this configuration, the sleeve is held away from the neck portion at a greater distance and thus the sleeve is prevented from everting or inverting into the neck portion. This embodiment may provide a more versatile arrangement as well when attaching a wider sleeve in, for example, a patient with a wider intestine, the structural element 190 can also be used to keep the sleeve open to allow food to enter the sleeve easier and continue on through the intestine.

FIGS. 21 to 24 illustrate various embodiments and shapes of an alternative structural element 190. The embodiments shown in FIGS. 21 to 24 all have the features of a structural element 190 providing additional strength to the overall structure of the anchor 110 and are collapsible.

In some embodiments, such as those shown in FIGS. 21 to 24, structural support can be provided to both the proximal flange and the distal flange with a single structural element 190 by providing a structural element 190 with a particular shape. For example, the structural element 190 may be shaped with the structural element 190 contoured through or oriented longitudinal to the neck portion and extending through at least one flange. The points of attachment on both the neck portion and the flanges are selected to enable compressive and expansive forces to be transferred between the flanges and the neck portion by the structural element 190.

In the embodiments illustrated in FIGS. 21 to 24, the structural element 190 traverses the neck portion of the anchor. The orientation and location of such a structural element 190 enables the structural element 190 to maintain the angle of each flange perpendicular to the neck portion. This allows each flange to resist circumferential compression while also preventing each flange from canting. The illustrated embodiments enable the anchor 110 to be collapsed into a shape that can be loaded into a small diameter tube for the purpose of delivering or retrieving the implant endoscopically in a human. Various structural features also enable the anchor 110 containing an alternative structural element 190 to be collapsed and provide a bias to the direction of collapse.

Figure 25:
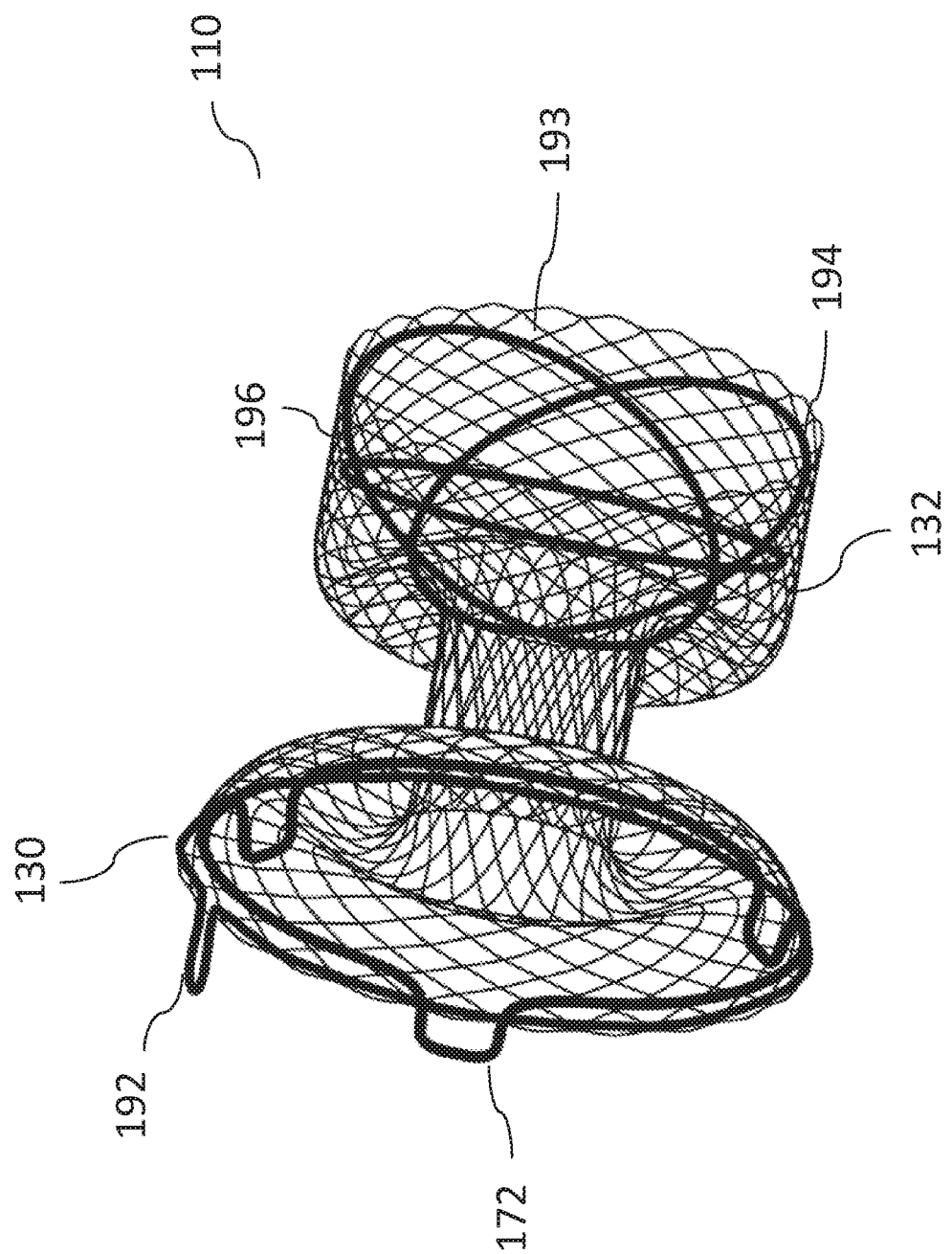
FIG. 25 is a perspective view of an exemplary pyloric implant with a proximal structural element and a distal structural element, according to some embodiments.

As shown in FIG. 25, in some embodiments, the anchor 110 has a distal structural element comprised of three rings 193, 194, 196 attached to the distal flange 132. The distal structural element 193, 194, 196 can be made from a metal such as Nitinol, MP35N, L605, Elgiloy, stainless steel or from a plastic such as PET, PEEK, or Delrin or other suitable material. In a preferred embodiment, the distal structural element 193, 194, 196 is made from superelastic Nitinol wire formed into the particular shape. In one example, a structural element was formed from three rings of Nitinol wire. If a structural element having a particular rigidity or stiffness is required, often the size and material that the stiffening element is made from can be used to control these properties. Typically, the Nitinol wire that has been used to form stiffening elements has a compressive and expansive strength that is a function of the diameter of the wire used to make the stiffening element.

The distal structural element 193, 194, 196 may be formed of material having a thickness in the range from 0.010 inch to about 0.040 inch, or any range in between such as from about 0.015 inch to about 0.030, from about 0.020 inch to about 0.025 inch. In an example embodiment, a distal structural element 193, 194, 196 comprised a plurality of rings formed from material having a thickness of about 0.020 inch, or about 0.51 mm. Generally, each of the three rings that form the distal structural element 193, 194, 196 have the same diameter which are in the range of from 1.0 inch to 2.0 inches, and any range within such as from about 1.2 inches to about 1.8 inches, and from about 1.3 inches to about 1.7 inches. In an example embodiment, the distal structural element 193, 194, 196 comprised material formed into rings each having a diameter of about 1.38 inches, or about 35.0 mm.

Figure 26:
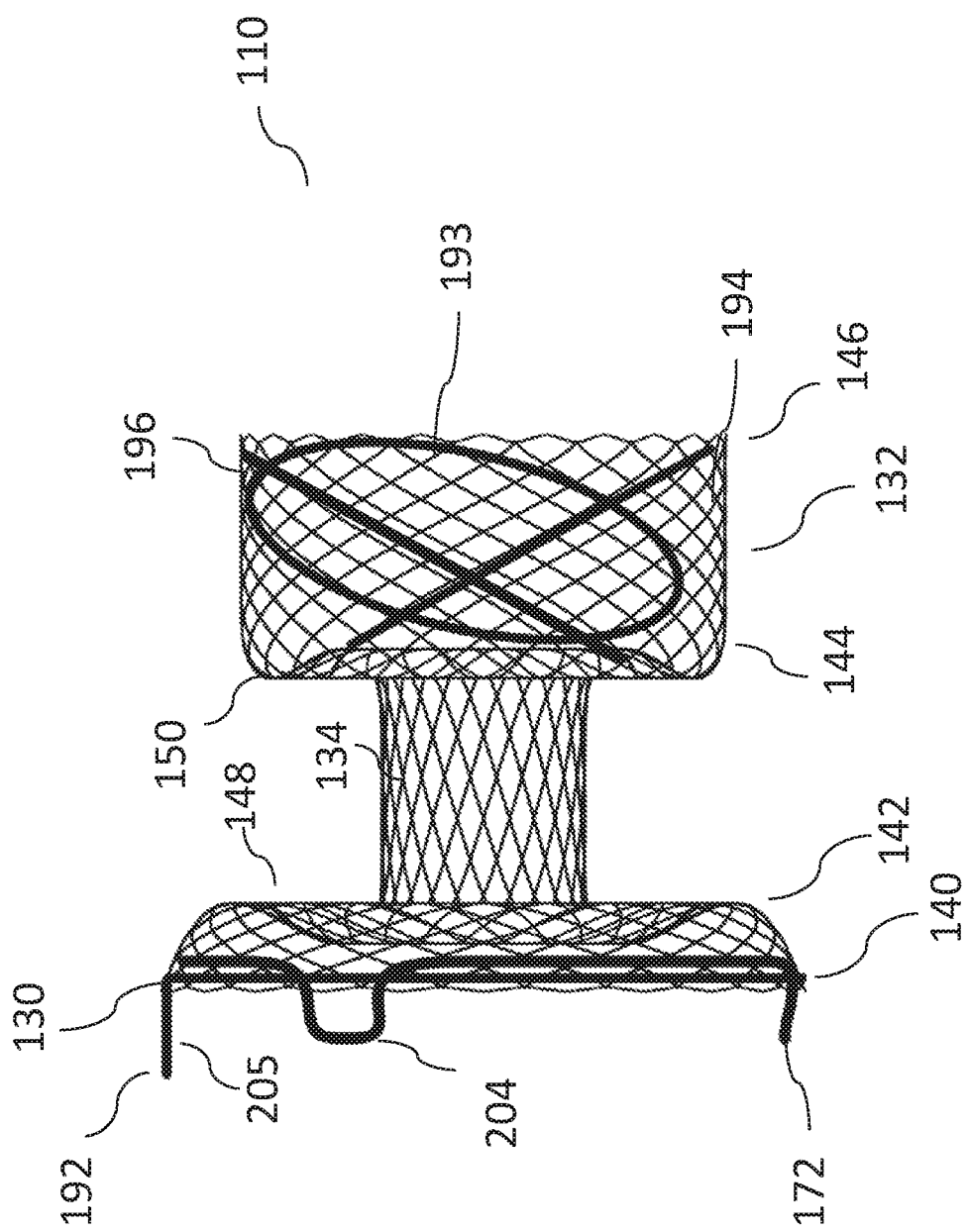
FIG. 26 is a side view of an exemplary pyloric implant with a proximal structural element and a distal structural element, according to some embodiments.

As shown in FIGS. 25 and 26, the three rings of the distal structural element 193, 194, 196 are arranged around the distal flange 132 and are attached to the distal flange 132 by being integrally woven into the flange material. The rings of the distal structural element 193, 194, 196 are attached by first weaving the formed wire of the rings though the braided structure of the distal flange 132 and then the wire ends are inserted into a sleeve and crimped or welded. FIG. 26 contains a side view of an example embodiment of the anchor 110, illustrating how each ring may be arranged with at least a portion of each ring attached to the distal flange distal end 146 and a portion attached to the distal flange distal wall 150. In still further embodiments, each ring may be attached with at least a portion of each ring closer to the distal flange proximal end 144 and a portion attached to the distal flange distal wall 150.

To provide structural support and to optimize the expansive force of the flanges, the orientation of the structural element or rings are arranged to provide any of a static radial force, a static longitudinal force or both. Often this requires the structural element to receive radial support from the neck portion or the wall of the anchor. In some embodiments, such as those shown in FIGS. 21 to 24, this is accomplished by providing a structural element with a particular shape. In some embodiments, the design of the structural element may incorporate a plurality of rings. The orientation of the rings relative to the wall or face of the flange can be designed to provide suitable static structure. This can be accomplished by placing the rings out-of-plane with the flange wall. In a structure incorporating rings for the structural element, the rings are generally attached to the implant at about four locations. The attachment locations are evenly spaced around the ring and enable the compressive and expansive forces to be transferred between the flanges and the structural element evenly.

As shown in FIGS. 25 and 26, in some embodiments the anchor 110 may have a proximal structural element 172 attached to the proximal flange 130. The proximal structural element 172 may also be referred to as a compression bias spring. The proximal structural element 172 may be constructed as a substantially circular frame having nodes 204. The proximal structural element 172 may be constructed from the same material that forms the distal structural element 193, 194, 196. The proximal structural element 172 may also provide structural support to the proximal flange 130. For example, the proximal structural element 172 generally has an overall frame that is compressible, yet also is rigid. The rigid proximal structural element 172 tends to impart additional strength to the proximal flange 130 and aids in keeping the proximal end 140 of the proximal flange 130 open. The proximal structural element 172 can be shaped to bias the collapse of the diameter of the anchor 110 for removal from a patient and for loading the device onto a delivery catheter for delivery within a patient.

As shown in FIGS. 25 and 26 in some embodiments, the anchor 110 may include a drawstring 192. The drawstring may be attached to the proximal flange 130. The drawstring 192 typically can be attached to the proximal flange 130 by weaving the drawstring 192 through the material of the proximal flange 130. As shown in FIG. 26, the drawstring may be weaved through the material of the proximal flange and have a portion of the drawstring forming a drawstring loop 205. For example, the drawstring 192 may be constructed from a string or suture that is weaved through alternating cells in the braided wire structure of the anchor 110. The draw string loop 205 allows the drawstring 192 to be attached to a retraction tool, for example by a hook or a clamp. In some embodiments, the drawstring 192 is simply a suture that is weaved through the proximal flange 130. The drawstring may be separate from the proximal structural element 172. The drawstring may be constructed from any range of suture material and may comprise a thin wire or cable. The drawstring 192 can be used to elastically contract the anchor 110 by connecting at least one loop 205 to a removal device (not shown) and by drawing into a sheath, for example a catheter. In some embodiments, the drawstring 192 allows the proximal flange 130 to collapse to the diameter of the neck portion 134.

Figure 27:
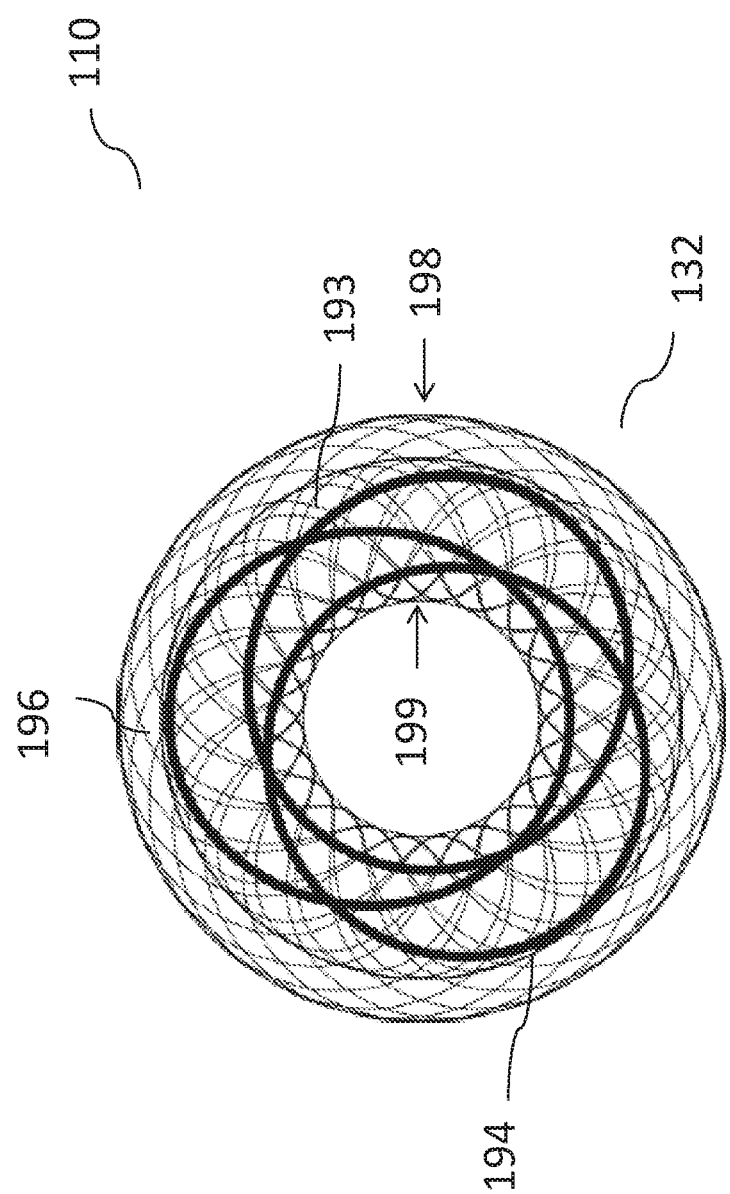
FIG. 27 is an axial view of an exemplary pyloric implant with a proximal structural element and a distal structural element, as viewed from the distal end, according to some embodiments.

FIG. 27 shows the anchor 110 from an axial perspective looking down the longitudinal direction from the distal end 146 of the distal flange 132. In some embodiments, the distal flange 132 has an outer circumference 198, defined by the outer most edge of the proximal end 144 or distal end 146 of the distal flange 132, and an inner circumference 199 defined by the location where the distal flange distal wall 150 meets the neck portion 134. In some embodiments, the inner circumference 199 of the distal flange is the same circumference as a circumference of the neck portion 134. As illustrated in FIG. 27, the distal structural element 193, 194, 196 may be formed by placing three rings at equal distances from each other around the distal flange 132 to provide pressure outward from an inner circumference 199, for example starting from the distal flange distal wall 150, and push outward against the outer circumference 198 of the distal flange 132.

Figure 28:
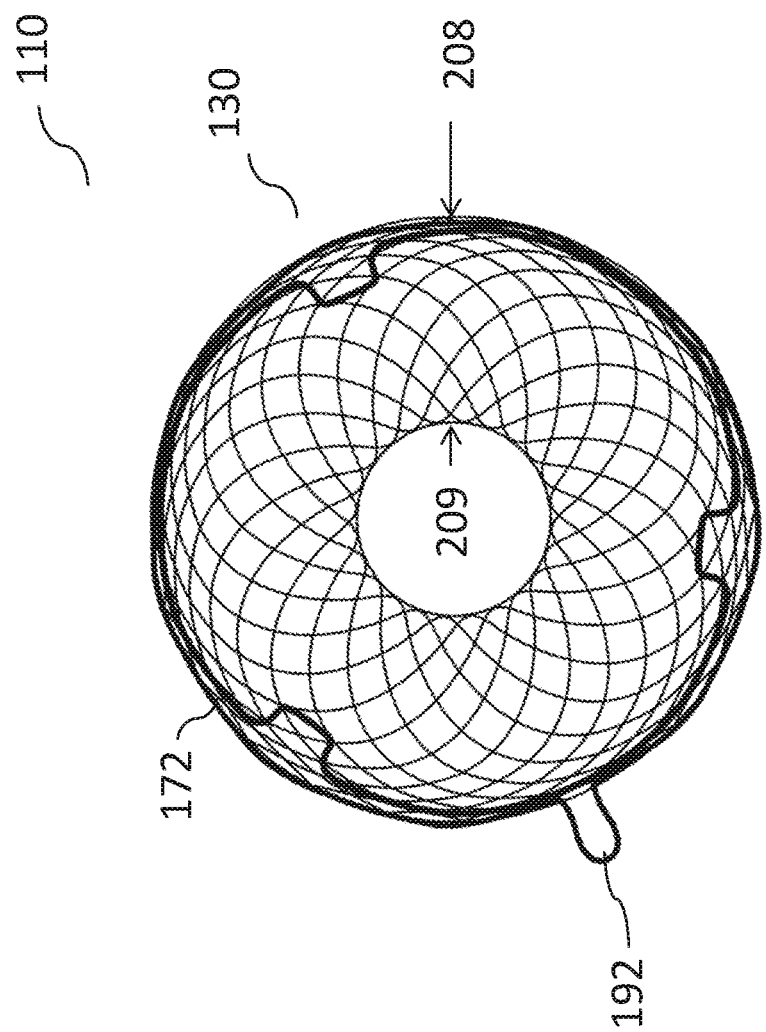
FIG. 28 is an axial view of an exemplary pyloric implant with a proximal structural element and a distal structural element, as viewed from the proximal end, according to some embodiments.

FIG. 28 illustrates the proximal structural element 172 and the drawstring 192 within the proximal flange 130 of the anchor 110 as viewed from an axial perspective looking down the longitudinal direction from the proximal end 140 of the proximal flange 130. In some embodiments, the proximal flange 130 has an outer circumference 208, defined by the outer most edge of the proximal end 140 or distal end 142 of the proximal flange 130, and an inner circumference 209 defined by the location where the proximal flange proximal wall 148 meets the neck portion 134 (shown in FIG. 26). In some embodiments, the inner circumference 209 of the proximal flange 130 is the same as a circumference of the neck portion 134.

Figure 29:
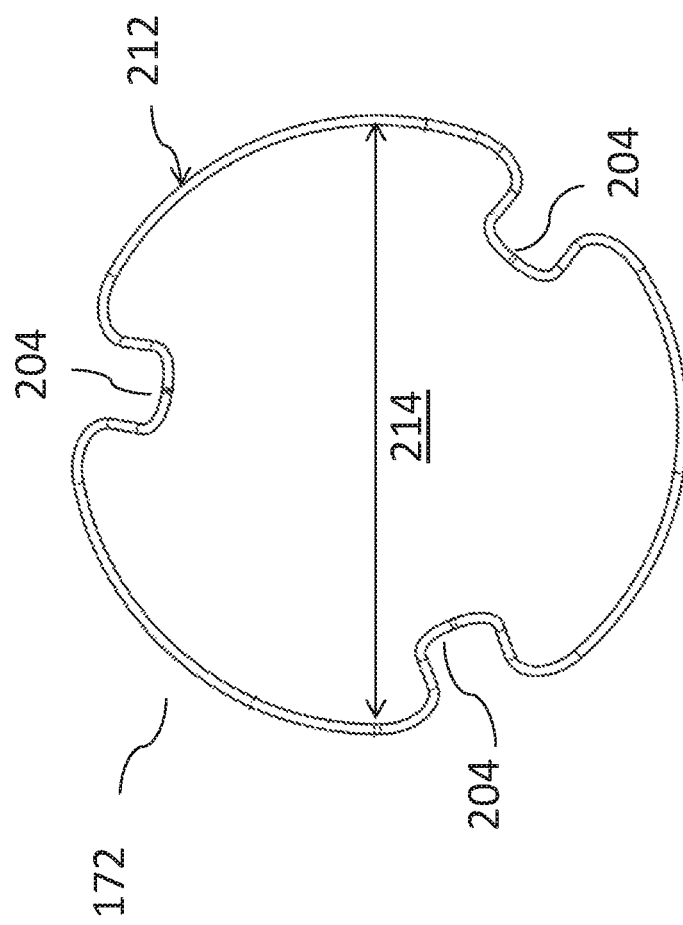
FIG. 29 is an axial view of an exemplary structural element that can be used on a flange of an implant, according to some embodiments.

FIG. 29 illustrates an embodiment of the proximal structural element 172 without the anchor, to illustrate an overall shape and structure. FIG. 29 shows the proximal structural element 172 as viewed from an axial perspective looking down the longitudinal direction and shows the proximal structural element 172 having a main body 212 that is substantially circular and having a diameter 214. The proximal structural element diameter 214 may be in the range of from 1.0 inch to 2.0 inches, and any range in between such as from about 1.3 inches to about 1.8 inches, or from about 1.5 inches to about 1.7 inches. In an example embodiment, the proximal structural element main body 212 comprised a ring having a diameter of about 1.57 inches, or about 40.0 mm.

The proximal structural element 172 may be formed of material having a thickness in the range from 0.015 inch to about 0.045 inch, or any range within such as from about 0.020 inch to about 0.035 inch, from about 0.025 inch to about 0.030 inch. In an example embodiment, a proximal structural element 172 was formed from material having a thickness of about 0.025 inch, or about 0.64 mm.

Figure 30A:
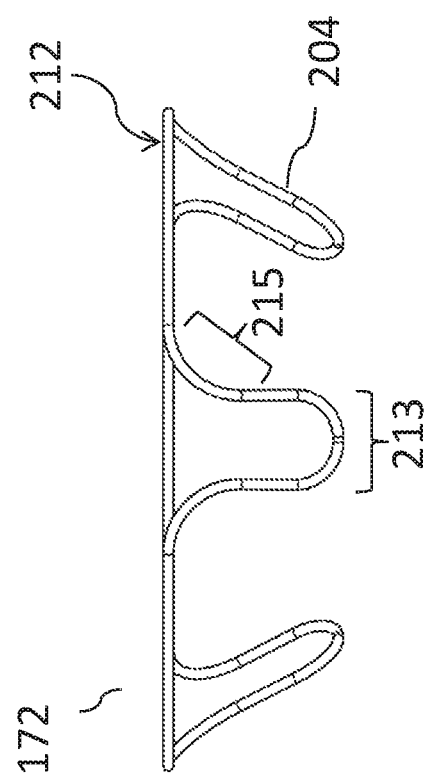
FIGS. 30A and 30B are a side view of an exemplary structural element that can be used on a flange of an implant, according to some embodiments.
Figure 30B:
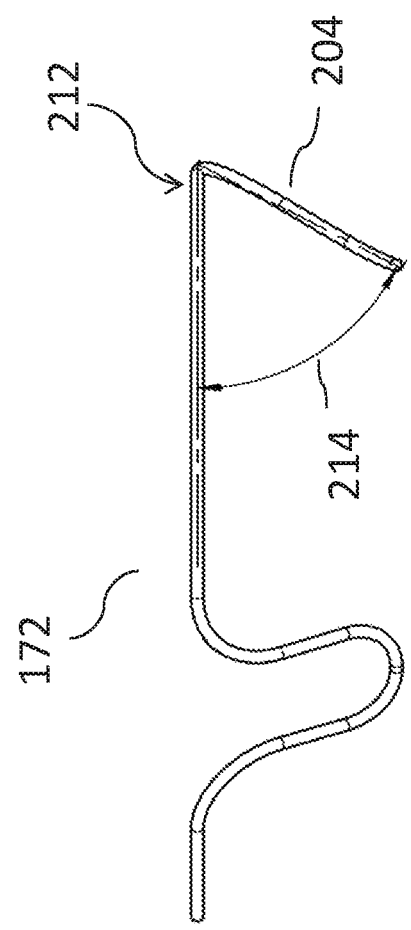

In some embodiments, attached to the main body 212 of the proximal structural element 172 is a plurality of nodes 204. As shown in FIGS. 30A and 30B, when viewed from the side, the proximal structural element main body 212 has an overall planar structure, with the nodes 204 extending from the plane of the main body 212. The nodes may be at an angle 214 to the plane of the main body 212, for example the nodes 204 may be formed to extend at a 60 degree angle from the main body 212. The nodes 204 may each have an outer loop 213 and an inner curve 215. The outer loop 213 allows a bias for the proximal structural element 172 to collapse radially in response to a compressive force. This action can be desirable for removal of the anchor from a patient and for loading the implant onto a delivery catheter for delivery within a patient. Additionally, the angle 214 helps to collapse the anchor in a uniform manner when the drawstring is pulled. The angle 214 of each node 204 allows for evenly distributed tension to be imparted to the main body 212 without forming a pinch point. The angle 214 also forms a shape that allows the anchor a bias toward a retracted configuration when tension is placed on the drawstring 172.

Figure 31:
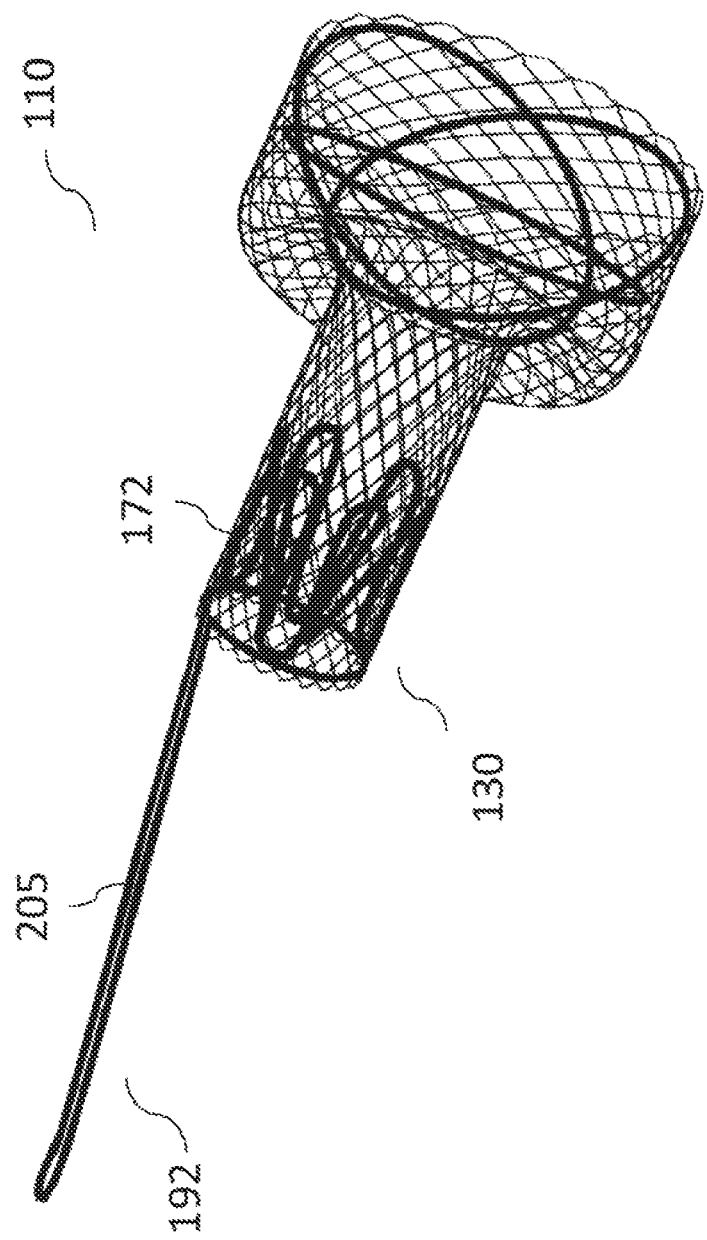
FIG. 31 is a side view of an exemplary pyloric implant with a distal structural element and a proximal structural element in a contracted configuration, according to some embodiments.

In some embodiments, the anchor 110 may be may be configured to collapse into a narrower size. For example, the anchor 110 may be collapsed into a narrower diameter for placement or removal from a patient. FIG. 31 shows the proximal flange 130 of the anchor 110 in the collapsed stage. In some embodiments the anchor can be collapsed by pulling the drawstring. The drawstring node 205 may be pulled away from the anchor 110, collapsing the proximal structural element 172. FIG. 31 shows the proximal flange 130 in a collapsed stage after the drawstring 192 has been pulled.

Figure 32:
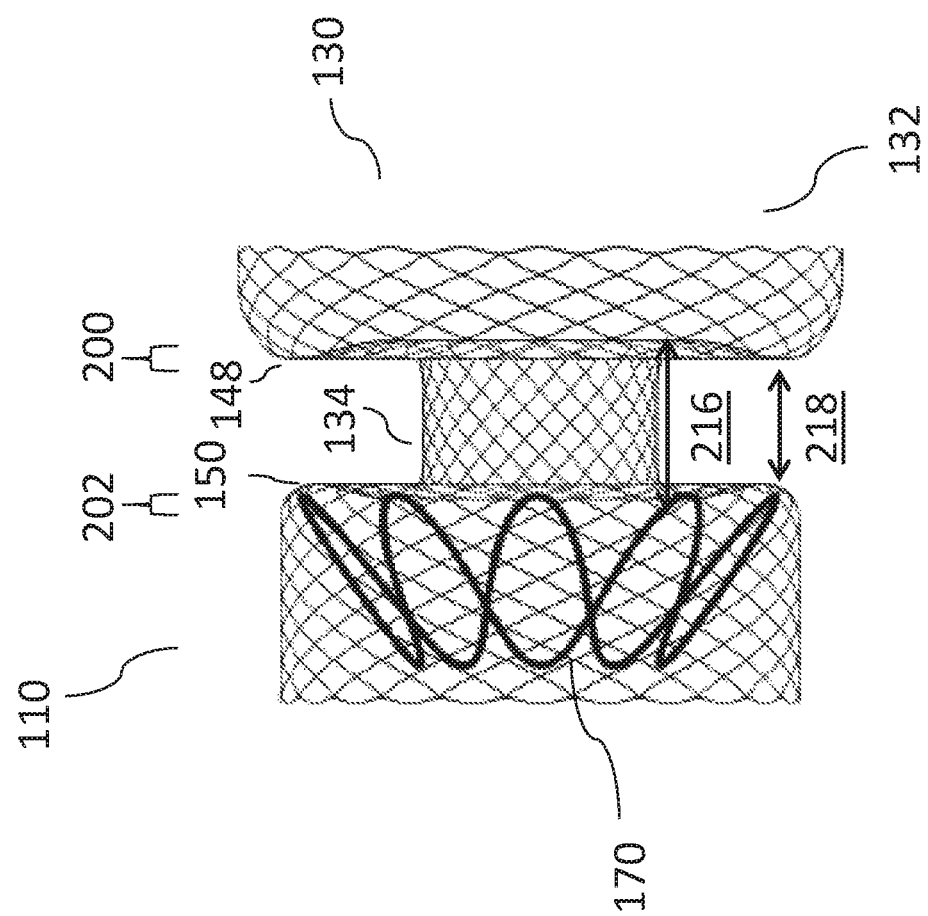
FIG. 32 is a side view of an exemplary pyloric implant, according to some embodiments.

As shown in FIG. 32, in some embodiments, the proximal flange wall 148 and the distal flange wall 150 may be constructed with a bias in relation to the central axis. The structural element 170 may also be configured to impart a bias on the distal flange wall 150. The proximal structural element, (not shown) may also impart a similar bias on the proximal flange wall 148. For example, the structural element 170 may be configured to impart a bias against the distal flange wall 150 in the proximal direction. For example, the distal structural element 170 may be configured to impart a bias against the distal flange wall 150 in the proximal direction. In other words, in some embodiments, the proximal flange wall 148 and the distal flange wall 150 may not be a completely flat configuration, but instead may have an angle, curve, or slope. As also shown in FIG. 32, the neck portion of the anchor has a length 216. In some embodiments, because of the slope, curve, or angle, of the proximal flange wall 148 and distal flange wall 150 the distance 218 between the outer circumference (208 in FIG. 28) of the proximal flange wall 148 and the outer circumference (198 in FIG. 27) of the distal flange wall 150 may be less than the length of the neck portion 216. As a result, the proximal flange wall 148 has a proximal gap 200 and the distal flange wall has a distal gap 202. The proximal gap 200 is defined by the difference in the longitudinal location of the proximal flange wall 148 at the outer circumference (208 in FIG. 28) and the inner circumference (209 in FIG. 28). The distal gap 202 is defined by the difference in the longitudinal location of the distal flange wall 150 at the outer circumference (198 in FIG. 27) and the inner circumference (199 in FIG. 27).

Figure 33:
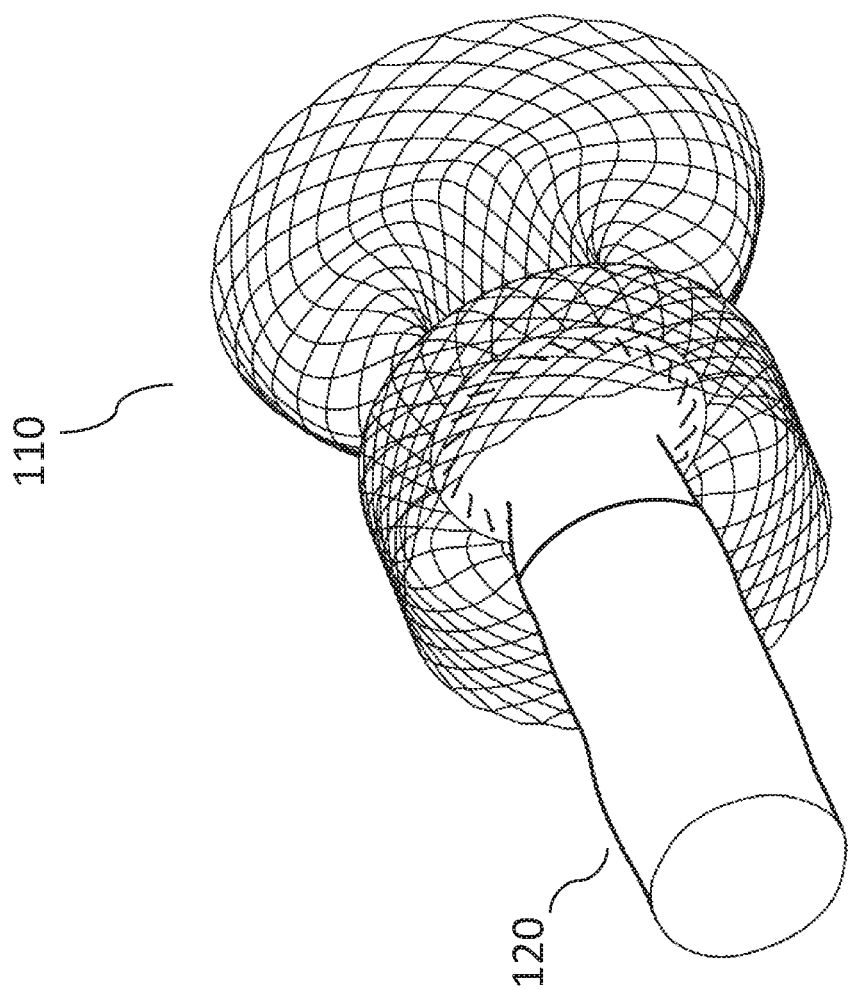
FIG. 33 is a perspective view of an exemplary implant having an intestinal bypass sleeve, according to some embodiments.
Figure 34:
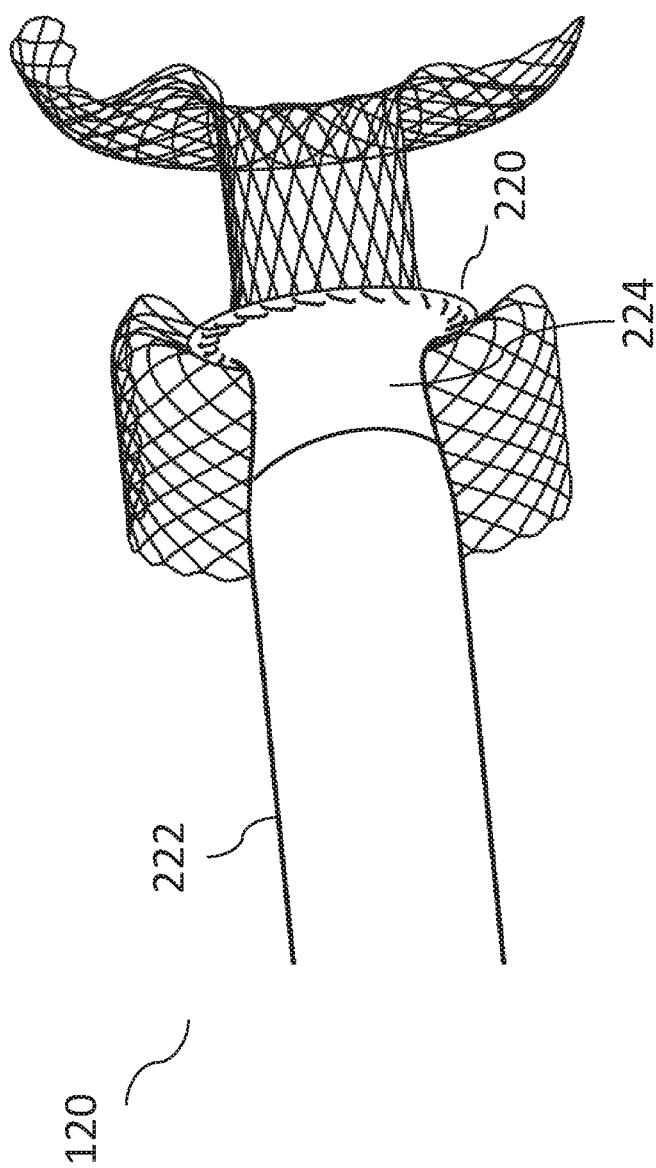
FIG. 34 is a perspective view of an exemplary implant having an intestinal bypass sleeve, according to some embodiments.

FIGS. 33 and 34 show an exemplary sleeve 120 that may be used in conjunction with an anchor. As shown previously in FIG. 2, the sleeve 120 may be attached to the anchor 110 and be placed within the small intestine 18. In various exemplary embodiments, the sleeve 120 is integrally formed with or coupled to the anchor 110. According to some embodiments, the sleeve 120 is removably or releasably coupled to the anchor 110.

As shown in FIG. 34, an overall schematic of a sleeve according to some embodiments includes a mouth 220, a sleeve body 222, and a neck 224 The sleeve body 222 diameter is generally sized to match the diameter of the human small intestine. The diameter decreases at the neck 224 to be consistent with the inner diameter of the anchor. This change in diameter also helps to prevent sleeve eversion in which the sleeve folds back into itself in response to an increase in pressure on the outside of the sleeve. According to various embodiments, the sleeve body has a thickness of between about 0.001 and about 0.015 inches. The sleeve neck 224 is intended to be thicker than the sleeve body 222, for example 0.005 inches versus 0.001 inches thick, to provide a second mechanism to prevent sleeve eversion. When the sleeve is subjected to an external pressure, the thicker neck 224 collapses and does not fold back on itself. This mechanism essentially creates a duck-bill valve.

The sleeve 120 can vary in length from 1.0-2.0 inches in length up to several feet. In some embodiments, the sleeve 120 bypasses the length of the duodenum up to the ligament of treitz. While various embodiments disclosed herein describe the intestinal bypass sleeve 120 as extending into the duodenum, in all such embodiments, it is also contemplated that the intestinal bypass sleeve 120 has a length sufficient to allow it to extend partially or fully into the jejunum. Often the length of the sleeve is dictated by the required mechanism of action. It has been shown that an effective sleeve length is one that allows it to reach the proximal jejunum; this location corresponds to the location of the ligament of Trietz. The length of the sleeve is determined based on the desired clinical outcome. Recent scientific research has indicated that a sleeve roughly 2 feet in length is sufficient to modify the transport and absorption of food and organ secretions within the small intestine, leading to remission of type 2 diabetes.

The intestinal bypass sleeve 120 may be made from a thin-walled polymer material such as silicone, polyurethane, polytetrafluoroethylene, fluorinated ethylene propylene, polyethylene, expanded polytetrafluoroethylene (ePTFE) or other suitable material. In exemplary embodiments, the wall thickness of the intestinal bypass sleeve 120 may be between 0.0006 inch and 0.010 inch thick. The intestinal bypass sleeve 120 may be made by extrusion, into a tubular form or a lay flat tubing, dip coated from a liquid solution, powder coated from fine particles of polymer or paste extruded and then stretched as is the case with ePTFE.

The gastrointestinal device thus described comprises an anchor configured to be implanted and remain within a pylorus of a patient. The gastrointestinal device may comprise an anchor having a flexible thin-walled sleeve attached to the distal end of the anchor. In some embodiments, secondary anchors may also anchor other portions of the thin-walled sleeve. The anchor may be placed within a pylorus of a patient to assist in opening a pylorus of the patient. The sleeve may be placed within the intestine of the patient and held in place by the anchor. The device thus described may function as follows.

As a person ingests food, the food enters the mouth, is chewed, and then proceeds down the esophagus and into the stomach. The food mixes with enzymes in the mouth and in the stomach. The stomach converts the food to a semi-fluid substance called chyme. The chyme enters the pyloric antrum and exits the stomach through the pylorus. The pylorus (or pyloric sphincter) is a band of muscle that functions to adjust the diameter of the pyloric orifice, which in turn effects the rate at which chyme exits the stomach. The pylorus (or phyloric sphincter or pyloric wall) also has a width (or thickness), which is the distance that the pylorus extends between the stomach and the duodenum.

A gastrointestinal implant placed within the pylorus of a patent can be employed to control the opening and closing of the pylorus to control the flow rate of chyme from the stomach to the intestine of the patient. An exemplary gastrointestinal implant has been formed that can assume both an expanded and contracted configuration. In an exemplary configuration, the implant has a neck portion that allows chyme to flow from the stomach to the intestine of a patient. The width of the neck portion can be designed to control the flow rate of chyme from the stomach to the intestine. The flow rate of chyme can optionally be modified depending on the suitable blood glucose levels of the patient.

The gastrointestinal implant may be held in place within a pylorus of a patient by using an anchor. The anchor comprises a proximal flange and a distal flange connected to the neck portion to anchor the neck portion in place. The proximal flange is configured to remain on the stomach side of a patient's pylorus and the distal flange is configured to remain on the intestinal side of a patient's pylorus. The widths of the proximal flange and distal flange in the expanded configuration are wider than the maximum diameter of the pylorus.

The length of the neck portion can be configured to provide an optimum fit within the pylorus of a patient while preventing the neck portion from agitating the tissue of the pylorus. It has been discovered that an optimum length of the neck portion reduces agitation of the tissue of the pylorus by the anchor by reducing contact between the proximal and distal flanges of the anchor and the pyloric wall. By creating the neck portion to be longer than the width of the pyloric wall, the proximal flange and distal flange are arranged such that they have minimal contact with the pylorus as the pylorus opens and closes. Additionally or alternatively, the shape of the proximal flange and distal flange can be formed to include a bias that reduces contact with the pylorus as the pylorus opens and closes. For example, the proximal flange and distal flange may be formed to provide a space between the proximal flange and distal flange and the pylorus.

The anchor may be formed from material having a hollow tubular braided structure that can assume a collapsed configuration for placement within and removal from a patient's digestive system. The hollow tubular braided structure also can assume an expanded configuration for suitable placement within a patient's digestive track. The anchor may include a structural element that provides additional structural support to the anchor and keeps the anchor in an expanded configuration yet also allows the anchor to be compressed for ease of placement within and extraction from a patient. For example, a structural element can be placed within the distal flange to provide structural support in the radial direction and thus prevent the distal flange from reverting into the stomach of a patient. Additionally or alternatively, a drawstring may be placed within the proximal flange to provide structural support in the radial direction and prevent the proximal flange from traveling into the intestine of a patient. Both the structural elements can be configured to be compressed into a collapsed configuration to allow the anchor to be placed within and removed from within a patient's digestive track. The neck portion of the anchor can be tailored to span the pylorus, and may be tailored to fit various patients of various dimensions. Additionally, the length of the neck portion can be tailored to extend past the pylorus to reduce a compressive force exerted by the flanges onto the pylorus. For example, the length of the neck portion can be designed to sit within the patient's anatomy without continuous contact with the walls of the duodenal bulb and pyloric antrum. The diameter of the neck portion can also be sized to allow food to pass from a patient's stomach to intestine yet remain narrow enough to prevent it from propping open the pylorus.

The small intestine is about 21 feet long in adults. The small intestine is comprised of three sections: the duodenum, jejunum, and ileum. The duodenum is the first portion of the small intestine and is typically 10.0-12.0 inches long. The duodenum is comprised of four sections: the superior, descending, horizontal and ascending. The duodenum ends at the ligament of treitz. The duodenal bulb is the portion of the duodenum which is closest to the stomach. Suitably designed sleeves can be sized wherein the length of the sleeve determines at what point the chyme is allowed to contact the intestine. The design and length of the sleeve also determines at what point food that is traveling through the sleeve comes into contact with digestive juices.

The gastrointestinal implant described here in can be placed within a patient's digestive track by inserting an endoscope through the mouth, esophagus and stomach to the pylorus. An over-the-wire sizing balloon is inserted through the working channel of the endoscope over a guidewire and is advanced across the pyloric opening. The balloon is inflated with saline or contrast media to a low pressure to open the pylorus and duodenum and allow measurement of the lumen diameter of the pyloric antrum, pylorus and duodenal bulb.

In some embodiments, blood glucose levels can be measured by a glucose sensor and the insulin infusion rates and optimum chyme flow rates can be set by the diameter of the neck portion. Currently diabetic patients monitor blood glucose levels and then based on their insulin levels inject themselves with insulin either with a syringe or with an infusion pump. Gastric emptying rates vary depending upon the composition of the food eaten. Sugars pass quickly from the stomach into the small intestine and protein and fats move from the stomach into the small intestine more slowly. Blood sugar control can be difficult to manage if the flow rate of chyme from the stomach to the small intestine is unpredictable and in the case of patients with gastroparesis the chyme flow rate can be very slow to zero. The disclosure herein described will allow for a tighter glucose level control by allowing more precise control of the flow rate of chyme into small intestine and modulating the flow rate of chyme base on blood glucose levels and insulin infusion rate.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A gastrointestinal implant for use within a pylorus, a duodenal bulb, and a duodenum of a patient, the implant having an expanded configuration and a contracted configuration and comprising:
an anchor having a longitudinal axis and including:
a proximal portion including a hollow tubular braided structure of wire and defining a cylinder having a proximal end, a distal end, and a first wall extending radially inward from the distal end of the proximal portion, wherein the first wall has an outer circumference and a first opening defining an inner circumference;
a neck portion including a cylinder having a proximal end attached to the first opening, a distal end, and a neck wall extending from the proximal end to the distal end;
a distal portion including a hollow tubular braided structure of wire and defining a cylinder having a proximal end, a distal end, an outer wall extending between the proximal end and the distal end, and a second wall extending radially inward from the proximal end of the distal portion, wherein the second wall has an outer circumference and a second opening defining an inner circumference and attached to the distal end of the neck portion; and
a plurality of rings attached to the distal portion, wherein each ring of the plurality of rings has a first section attached to the outer wall of the distal portion and a second section attached to at least one of the second wall and the neck portion, and wherein each ring of the plurality of rings is oriented in a plane that is offset from and intersects one or more planes of one or more other rings of the plurality of rings.

2. The gastrointestinal implant of claim 1, wherein the first section of each ring of the plurality of rings is attached along a circumference of the outer wall and the second section of each ring of the plurality of rings is attached along a circumference of at least one of the second wall and the neck portion.

3. The gastrointestinal implant of claim 1, wherein each ring of the plurality of rings has a round shape, a rectangular shape, a square shape or an elliptical shape.

4. The gastrointestinal implant of claim 1, wherein the first wall defines a concave surface that is curved between the outer circumference and the inner circumference of the first wall.

5. The gastrointestinal implant of claim 1, wherein the first wall defines a concave surface that is curved between the outer circumference of the first wall and the proximal end of the neck portion with a curve perpendicular to the longitudinal axis.

6. The gastrointestinal implant of claim 1, wherein the second wall defines a concave surface that is curved between the outer circumference and the inner circumference of the second wall.

7. The gastrointestinal implant of claim 1, wherein the second wall defines a concave surface that is curved between the outer circumference of the second wall and the distal end of the neck portion with a curve perpendicular to the longitudinal axis.

8. The gastrointestinal implant of claim 1, wherein the first section of each ring of the plurality of rings is attached to a first portion of the distal portion and the second section of each ring of the plurality of rings is attached to a second portion of the distal portion, such that the first portion and the second portion are 180 degrees apart.

9. The gastrointestinal implant of claim 1, wherein the first section of each ring of the plurality of rings is attached to a first portion of the distal portion adjacent the distal end of the distal portion and the second section of each ring of the plurality of rings is attached to a second portion of the distal portion adjacent the inner circumference of the second wall.

10. The gastrointestinal implant of claim 1, wherein each ring of the plurality of rings is oriented in a plane such that the rings of the plurality of rings are nonparallel to one another.

11. A gastrointestinal implant for use within a pylorus, a duodenal bulb, and a duodenum of a patient, the implant having an expanded configuration and a contracted configuration and comprising:
an anchor having a longitudinal axis and including:
a proximal portion including a hollow tubular braided structure of wire and defining a cylinder having a proximal end, a distal end, and a first wall extending radially inward from the distal end of the proximal portion, wherein the first wall has an outer circumference and a first opening defining an inner circumference;

a neck portion including a cylinder having a proximal end attached to the first opening, a distal end, and a neck wall extending from the proximal end to the distal end;

a distal portion including a hollow tubular braided structure of wire and defining a cylinder having a proximal end, a distal end, an outer wall extending between the proximal end and the distal end, and a second wall extending radially inward from the proximal end of the distal portion, wherein the second wall has an outer circumference and a second opening defining an inner circumference and attached to the distal end of the neck portion; and a plurality of rings attached to the distal portion, each ring of the plurality of rings has a first section attached to the outer wall of the distal portion and a second section attached to at least one of the second wall and the neck portion, wherein each ring of the plurality of rings is oriented in a plane, and the first section of each ring of the plurality of rings is attached to a first portion of the distal portion adjacent the outer circumference of the second wall and the second section of each ring of the plurality of rings is attached to a second portion of the distal portion adjacent the inner circumference of the second wall.

12. The gastrointestinal implant of claim 11, wherein the first wall defines a concave surface that is curved between the outer circumference and the inner circumference of the first wall.

13. The gastrointestinal implant of claim 11, wherein the second wall defines a concave surface that is curved between the outer circumference and the inner circumference of the second wall.

14. The gastrointestinal implant of claim 11, wherein the first section of each ring of the plurality of rings is attached to the first portion of the distal portion and the second section of each ring of the plurality of rings is attached to the second portion of the distal portion, such that the first portion and the second portion are 180 degrees apart.

15. The gastrointestinal implant of claim 11, wherein each ring of the plurality of rings is oriented in a plane such that the rings of the plurality of rings are nonparallel to one another.

16. A gastrointestinal implant for use within a pylorus, a duodenal bulb, and a duodenum of a patient, the implant having an expanded configuration and a contracted configuration and comprising:

an anchor having a longitudinal axis and including:

a proximal portion including a hollow tubular braided structure of wire and defining a cylinder having a proximal end, a distal end, and a first wall extending radially inward from the distal end of the proximal portion, wherein the first wall has an outer circumference and a first opening defining an inner circumference;

a neck portion including a cylinder having a proximal end attached to the first opening, a distal end, and a neck wall extending from the proximal end to the distal end;

a distal portion including a hollow tubular braided structure of wire and defining a cylinder having a proximal end, a distal end, an outer wall extending between the proximal end and the distal end, and a second wall extending radially inward from the proximal end of the distal portion, wherein the second wall has an outer circumference and a second opening defining an inner circumference and attached to the distal end of the neck portion; and a plurality of rings attached to the distal portion, wherein each ring of the plurality of rings is oriented in a plane, and the plurality of rings includes at least three rings, wherein each ring of the at least three rings is attached along a circumference of the outer wall at a location about 120 degrees apart from each of the other rings of the at least three rings.

17. The gastrointestinal implant of claim 16, wherein a first section of each ring of the plurality of rings is attached to a first portion of the distal portion adjacent the outer circumference of the second wall and a second section of each ring of the plurality of rings is attached to a second portion of the distal portion adjacent the inner circumference of the second wall.

18. The gastrointestinal implant of claim 16, wherein the first wall defines a concave surface that is curved between the outer circumference and the inner circumference of the first wall.

19. The gastrointestinal implant of claim 16, wherein the second wall defines a concave surface that is curved between the outer circumference and the inner circumference of the second wall.

20. The gastrointestinal implant of claim 16, wherein a first section of each ring of the plurality of rings is attached to a first portion of the distal portion and a second section of each ring of the plurality of rings is attached to a second portion of the distal portion, such that the first portion and the second portion are 180 degrees apart.

* * * * *